US009758553B2

(12) United States Patent
Sethuraman et al.

(10) Patent No.: US 9,758,553 B2
(45) Date of Patent: Sep. 12, 2017

(54) YEAST STRAIN FOR THE PRODUCTION OF PROTEINS WITH TERMINAL ALPHA-1,3-LINKED GALACTOSE

(71) Applicant: MERCK SHARP & DOHME CORP., Rahway, NJ (US)

(72) Inventors: Natarajan Sethuraman, Hanover, NH (US); Robert C. Davidson, Enfield, NH (US); Terrance A. Stadheim, Lebanon, NH (US); Stefan Wildt, Lebanon, NH (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/322,341

(22) Filed: Jul. 2, 2014

(65) Prior Publication Data

US 2014/0314797 A1    Oct. 23, 2014

Related U.S. Application Data

(62) Division of application No. 12/995,284, filed as application No. PCT/US2009/045446 on Dec. 3, 2009, now abandoned.

(60) Provisional application No. 61/130,422, filed on May 30, 2008.

(51) Int. Cl.
    *C07K 14/435*    (2006.01)
    *C12N 15/80*     (2006.01)
    *C12P 21/00*     (2006.01)

(52) U.S. Cl.
    CPC ............ *C07K 14/435* (2013.01); *C12N 15/80* (2013.01); *C12P 21/005* (2013.01)

(58) Field of Classification Search
    CPC ...... C07K 14/435; C12N 15/80; C12P 21/005
    See application file for complete search history.

(56) References Cited

U.S. PATENT DOCUMENTS

| | | |
|---|---|---|
| 6,264,957 B1 | 7/2001 | Collins et al. |
| 6,361,775 B1 | 3/2002 | Galili et al. |
| 7,029,872 B2 | 4/2006 | Gerngross et al. |
| 7,129,342 B1 | 10/2006 | Bukh et al. |
| 7,449,308 B2 | 11/2008 | Gerngross et al. |
| 7,465,577 B2 | 12/2008 | Bobrowicz et al. |
| 7,638,323 B2 | 12/2009 | Holgersson et al. |
| 7,795,002 B2 | 9/2010 | Davidson et al. |
| 2002/0128221 A1 | 9/2002 | Schiff |
| 2004/0002585 A1 | 1/2004 | Holgersson et al. |

(Continued)

FOREIGN PATENT DOCUMENTS

| | | |
|---|---|---|
| WO | WO0200879 | 1/2002 |
| WO | 03-056914 A1 | 7/2003 |

(Continued)

OTHER PUBLICATIONS

Wildt et al., The Humanization of N-Glycosylation Pathways In Yeast., Nature Reviews (2005), vol. 3, pp. 119-128.*

(Continued)

*Primary Examiner* — Alexander Kim

(57) ABSTRACT

Lower eukaryotic host cells have been engineered to produce glycoprotein having at least one terminal α-galactosyl epitope. The glycoproteins are useful for the production of highly antigenic glycoprotein compositions with advantages for the production of vaccines.

6 Claims, 15 Drawing Sheets

(56) References Cited

U.S. PATENT DOCUMENTS

| | | |
|---|---|---|
| 2004/0018590 A1 | 1/2004 | Gerngross et al. |
| 2004/0137580 A1 | 7/2004 | Holgersson et al. |
| 2005/0170452 A1 | 8/2005 | Wildt et al. |
| 2006/0024292 A1 | 2/2006 | Gerngross et al. |
| 2006/0040353 A1 | 2/2006 | Davidson et al. |
| 2007/0014775 A1 | 1/2007 | Link et al. |
| 2009/0060930 A1 | 3/2009 | Mautino et al. |

FOREIGN PATENT DOCUMENTS

| | | |
|---|---|---|
| WO | 03056914 A1 | 7/2003 |
| WO | WO2005106010 | 11/2005 |
| WO | 2006-014683 A2 | 2/2006 |
| WO | 2006014683 A2 | 2/2006 |
| WO | 2008057235 A2 | 5/2008 |
| WO | WO2008/057235 | 5/2008 |
| WO | 2008-118487 A2 | 10/2008 |
| WO | 2008118487 A2 | 10/2008 |
| WO | WO2008/118487 | 10/2008 |
| WO | 2012135313 A1 | 10/2012 |
| WO | WO2012/135313 | 10/2012 |
| WO | 2012158932 A2 | 11/2012 |
| WO | WO2012/158932 | 11/2012 |

OTHER PUBLICATIONS

P32906 (last viewed on Apr. 2, 2014).*
Endoplasmic Reticulum, Golgi Apparatus, and Lysosomes (last viewed on Mar. 14, 2016).*
UniProKB Q548W5 (last viewed on Mar. 15, 2016).*
Henion, T R; Macher, B A; Anaraki, F; Galili. Defining the minimal size of catalytically active primate alpha 1,3 galactosyltransferase: structure-function studies on the recombinant truncated enzyme. Glycobiology 4(2):193-201; Apr. 1994; Oxford University Press.
Roy BB, Jinno-Oue A, Shinagawa M, Shimizu A, Tamura K, Shimizu N, Tanaka A, Hoshino H. Isolation of the feline alpha1,3-galactosyltransferase gene, expression in transfected human cells and its phylogenetic analysis. J. Exp. Zool. B. Mol. Dev. Evol. Jan. 15, 2006;306(1):59-69.
Simon G. Taylor, Ian F.C. McKenzie, and Mauro S. Sandrin. Characterization of the rat $\alpha(1,3)$galactosyltransferase: evidence for two independent genes encoding glycosyltransferases that synthesize Gal$\alpha$(1,3)Gal by two separate glycosylation pathways. Glycobiology 13(5): 327-337 (2003).
Wiggins CA, Munro S.. Activity of the yeast MNN1 alpha-1,3-mannosyltransferase requires a motif conserved in many other families of glycosyltransferases. Proc. Natl. Acad. Sci. U S A. Jul. 7, 1998;95(14):7945-50.
Invitrogen manual: pGAPZ A, B, and C; pGAPZ$\alpha$ A, B, and C; Pichia expression vectors for constitutive expression and purification of recombinant proteins. Catalog Nos. V200-20 and V205-20. (Sep. 3, 2002).
Yasunori Chiba, Misa Suzuki, Satoshi Yoshida, Aruto Yoshida, Hiroshi Ikenaga, Makoto Takeuchi, Yoshifumi Jigami, and Eiji Ichishimai. Production of Human Compatible High Mannose-type (Man$_5$GlcNAc$_2$) Sugar Chains in Saccharomyces cerevisiae. J. Biol. Chem. 273(41): 26298-26304 (1998).
Smith DF, Larsen RD, Mattox S, Lowe JB, Cummings RD. Transfer and expression of a murine UDP-Gal:beta-D-Gal-alpha 1,3-galactosyltransferase gene in transfected Chinese hamster ovary cells. Competition reactions between the alpha 1,3-galactosyltransferase and the endogenous alpha 2,3-sialyltransferase. J Biol Chem. Apr. 15, 1990;265(11):6225-34.
Stults CL, Macher BA, Bhatti R, Srivastava OP, Hindsgaul O. Characterization of the substrate specificity of alpha1,3galactosyltransferase utilizing modified N-acetyl-lactosamine disaccharides. Glycobiology. Jul. 1999;9(7):661-8.
Larsen RD, Rajan VP, Ruff MM, Kukowska-Latallo J, Cummings RD, Lowe JB. Isolation of a cDNA encoding a murine UDPgalactose:beta-D-galactosyl-1,4-N-acetyl-D-glucosaminide alpha-1,3-galactosyltransferase: expression cloning by gene transfer. Proc Natl Acad Sci U S A. Nov. 1989;86(21):8227-31.
Joziasse DH, Shaper JH, Van den Eijnden DH, Van Tunen AJ, Shaper NL. Bovine alpha 1-3-galactosyltransferase: isolation and characterization of a cDNA clone. Identification of homologous sequences in human genomic DNA. J Biol Chem. Aug. 25, 1989;264(24):14290-7.
Joziasse DH, Shaper NL, Kim D, Van den Eijnden DH, Shaper JH. Murine alpha 1,3-galactosyltransferase. A single gene locus specifies four isoforms of the enzyme by alternative splicing. J Biol Chem. Mar. 15, 1992;267(8):5534-41.
Hamilton SR, Gerngross TU. Glycosylation engineering in yeast: the advent of fully humanized yeast. Curr Opin Biotechnol. Oct. 2007;18(5):387-92. Epub Oct. 24, 2007.
Kainuma et al., Coexpression of $\alpha$1,2 galactosyltransferase and UDP-galactose transporter efficiently galactosylates N-and 0-glycans in Saccharomyces cerevisiae, Glycobiology., 1999, vol. 9, pp. 113-141.
Dole et al., Crystallization and Preliminary X-Ray Analysis of the Class 1 $\alpha$1,2-Mannosidase from Saccharomyces cerevisiae, Journal of Structural Biology (1997), vol. 120, Issue 1, pp. 69-72.
Chen et al., Synthesis of $\alpha$-gal epitopes (Gal$\alpha$1-3Gal$\beta$1-4GlcNAc-R) on human tumor cells by recombinant $\alpha$1,3galactosyltransferase production in Pichia pastoris, Glycobiology, 2001, vol. 11, pp. 577-586.
Guo et al., Protein tolerance to random amino acid change, 2004, Proc. Natl. Acad. Sci. USA 101: 9205-9210.
Lazar et al., Transforming Growth Factor $\alpha$: Mutation of Aspartic Acid 47 and Leucine 48 Results in Different Biological Activity, 1988, Mol. Cell. Biol. 8:1247-1252.
Hill et al., Functional Analysis of conserved Histidines in ADP-Glucose Pyrophosphorylase from Escherichia coli, 1998, Biochem. Biophys. Res. Comm. 244:573-577.
Wacey et al., Disentangling the perturbational effects of amino acid substitutions in the DNA-binding domain of p53, Hum Genet, 1999, vol. 104, pp. 15-22.
Zhang et al., Proteomics; 7:1379-1390 (2007).
Abdel-Motal et al., J. Virology, 80:6943-6951 (2006).
Abdel-Motal et al., J Virology, 81:9131-9141 (2007).
Anderton et al., Infection and Immunity, 72:2035-2044 (2004).
Bobrowicz et al., Glycobiology; 14:757-66 (2004).
Caldas et al., Protein Engineering, 13:353-360 (2000).
Camus et al., Microbiology 148:2967-2973 (2002).
Carter et al., J. Virol. 80: 4664-72 (2006).
Chang et al., J.Agric. Food Chem. 54:815-822 (2006).
Chen et al., J. Biol. Chem. 275:31594-31600 (2000).
Choi et al., PNAS 100:5022-5027 (2003).
Cloeckaert et al., Clinical and Diagnostic Laboratory Immunology; 6:627-629 (1999).
Dunn et al., PNAS, 100:14223-14228 (2003).
Folks, Nature Medicine 4:16-17 (1998).
Foxwell et al., Microbiol Mol Biol Rev, 62:294-308 (1998).
Galili et al, J Biol Chem, 263:17755-17762 (1988).
Galili et al., Blood, 82:2485-2493 (1993).
Hamilton et al., Science; 301:1244-6. (2003).
Henion et al., Vaccine, 15:1174-1182 (1997).
Lo et al., Clinical Infectious Diseases, 36:1246-53 (2003).
Marks et al., J. Mol. Biol. 222:581-596 (1991).
McCauley and Mahy, Biochem. J., 211:281-294 (1983).
McKevitt et al., Infection and Immunity, 73:4445-4450 (2005).
Ratner et al., Nature 313:277 (1985).
Russell, J. General Virology 81:2573-2604 (2000).
Schmaljohn et al., J. Gen. Virol. 69:1949-1955 (1988).
Svitkin et al., J. Virology; 79:6868-6881 (2005).
Webster et al., J. Histochem Cytochem 54:829-842 (2006).
Whitley and Roizman, J. Clin. Invest. 110: 145-151 (2002).
Wu et al., J. Bacteriol. 187:4720-4727 (2005).
Galili, Can. Immunol. Immunother. 53:935-945 (2004).
Galili et al., Vaccine 14:321-328 (1996).
Unfer et al., Can. Res. 63:987-993 (2003).

(56) References Cited

OTHER PUBLICATIONS

Sharma et al. Reduction in the level of Gal (alpha1, 3) Gal in transgenic mice and pigs by the expression of an alpha (1,2) fucosyltransferase. Proc Natl Acad Sci U S A. Jul. 9, 1996;93 (14) :7190-7195.
Macher et al. The Galalpha1,3Galbeta1,4GlcNAc-R (alpha-Gal) epitope: a carbohydrate of unique evolution and clinical relevance. Biochim Biophys Acta. Feb. 2008; 1780(2) :75-88. Epub Nov. 22, 2007.
U.S. Appl. No. 12/995,284, filed Nov. 20, 2010.
Chen, et al., Changing the Donor Cofactor of Bovine alpha1,3-Galactosyltransferase by Fusion with UDP-galactose 4-Epimerase, The Journal of Biological Chemistry, vol. 275, No. 41, Issue of Oct. 13, pp. 31594-31600, 2000.
Choi, et al., Use of combinatorial genetic libraries to humanize N-linked glycosylation in the yeast *Pichia pastoris*, Proceedings of the National Academy of Sciences, vol. 100, No. 9, pp. 5022-5027, 2003.
U.S. Appl. No. 12/995,284, filed Nov. 30, 2010.

\* cited by examiner

```
222 F C M D V D Q V F Q D K F G V E T L G E S V A Q L Q A W W Y K A D P N D F T Y E  BtAlpha1,3GalT
238 F C M D V D Q V F Q D S F G V E T L G Q S V A Q L Q A W W Y K A D P D E F T Y E  CfAlpha1,3GalT
225 F C M D V D Q V F Q N N F G V E T L G Q S V A Q L Q A W W Y K A H P D E F T Y E  SsAlpha1,3GalT
225 F C M D V D Q V F Q D N F G V E T L G Q L V A Q L Q A W W Y K A S P E K F T Y E  MmalphaGalTp 262 R R K E S A A Y I P F G E G D F Y Y H A A I F G G T P T Q V L N I T Q E C F K G  BtAlpha1,3GalT
278 R R K E S A A Y I P F G Q G D F Y Y H A A I F G G T P T Q V L N I T Q E C F K G  CfAlpha1,3GalT
265 R R K E S A A Y I P F G Q G D F Y Y H A A I F G G T P T Q V L N I T Q E C F K G  SsAlpha1,3GalT
265 R R E L S A A Y I P F G E G D F Y Y H A A I F G G T P T H I L N L T R E C F K G  MmalphaGalTp 302 I L K D K K N D I E A Q W H D E S H L N K Y F L L N K P T K I L S P E Y C W D Y  BtAlpha1,3GalT
318 I L Q D K K N D I E A E W H D E S H L N K Y F L L N K P T K I L S P E Y C W D Y  CfAlpha1,3GalT
305 I L Q D K E N D I E A E W H D E S H L N K Y F L L N K P T K I L S P E Y C W D Y  SsAlpha1,3GalT
305 I L Q D K H D I E A Q W H D E S H L N K Y F L F N K P T K I L S P E Y C W D Y  MmalphaGalTp 342 H I G L P A D I K L V K M S W Q T K E Y N V V R N N V                            BtAlpha1,3GalT
358 H I G L P S D I K T V K I S W Q T K E Y N L V R N N T                            CfAlpha1,3GalT
345 H I G M S V D I R I V K I A W Q K K E Y N L V R N N I                            SsAlpha1,3GalT
345 Q I G L P S D I K S V K V A W Q T K E Y N L V R N N V                            MmalphaGalTp
```

Percent Identity

| | 1 | 2 | 3 | 4 | |
|---|---|---|---|---|---|
| 1 | ■ | 85.1 | 82.6 | 73.1 | BtAlpha1,3GalT |
| 2 | 16.0 | ■ | 84.4 | 76.5 | CfAlpha1,3GalT |
| 3 | 16.8 | 15.0 | ■ | 73.6 | SsAlpha1,3GalT |
| 4 | 32.7 | 26.5 | 29.9 | ■ | MmalphaGalTp |
| | 1 | 2 | 3 | 4 | |

Bt = Bos taurus
Cf = Canis familiaris
Ss = Sus scrofa
Mm = Mus musculus

YEAST STRAIN FOR THE PRODUCTION OF PROTEINS WITH TERMINAL ALPHA-1,3-LINKED GALACTOSE

This application is a divisional of U.S. patent application Ser. No. 12/995,284, filed Nov. 30, 2010; which is the U.S. national phase, filed under 35 U.S.C. §371, of International Application No. PCT/US2009/45446, filed May 28, 2009; which claims the benefit of U.S. Provisional Patent Application No. 61/130,422, filed May 30, 2008; each of which is herein incorporated by referenced in its entirety.

FIELD OF THE INVENTION

The present invention relates to the field of molecular biology, in particular the invention is concerned with yeast strains genetically engineered to produce N-glycans with the predominant terminal sugar structure Gal-α1,3-Gal-β1,4-GlcNAc-R

BACKGROUND OF THE INVENTION

All mammals except humans and certain other primates contain glycoproteins that have terminal alpha-1,3-galactosyl (alpha-gal) glycan structures resulting from the activity of the enzyme alpha-1,3-galactosyl transferase (Galili et al, J Biol Chem, 263:33, 1988). The enzyme adds a galactose residue to terminally located beta-1,4-linked galactose residues. Beta-1,4-linked galactose residues are found at the termini of many N-glycans of mammals, including those of humans.

The human immune system has adapted natural immunity to quickly respond to the presence of terminal alpha-gal residues. Approximately one percent of circulating IgGs are directed against the alpha-1,3-galactose epitope (Galili et al, Blood, 82:8, 1993). Antigens that exhibit this epitope are recognized by circulating antibodies, resulting in complement activation, and the efficient activation of antigen-presenting cells via an Fcγ receptor-mediated pathway and the stimulation of a cytotoxic T-cell response. Targeting an immune complex to antigen presenting cells has been shown to reduce the amount of antigen required to elicit a T-cell response.

Current recombinant vaccines generally suffer from a lack of specific immunogenic response. Furthermore, current vaccines often require general immune stimulators known as adjuvants to elicit a sustained cytotoxic T-cell response. In a limited demonstration, a protein-based vaccine with N-glycans containing terminal α-1,3-galactose has been reported to improve the immunogenicity of such a molecule. (Abdel-Motal et al, J Virology, 80:14, 2006; Abdel-Motal et al, J Virology, 81:17, 2007.) This may be because humans have a high level of circulating antibodies directed against α-1,3-galactose residues. Moreover, because these proteins may be able to stimulate antigen presentation via antibody-directed Fc-gamma mediated signaling, they may reduce the need for non-specific adjuvants. The current state of the art only allows for production of such a vaccine by producing the protein with terminal sialic acid structures (e.g. NANA), then removing the NANA residues in vitro by enzymatic digest to expose the β-1,4 linked galactose residues, and subsequently adding terminal α-1,3-galactose through enzymatic addition (see, Galili, U.S. Pat. No. 6,361,775). This process is expensive, cumbersome, and not easily scalable. Attempts have been made to produce alpha-gal epitopes on viral proteins such as influenza virus hemagglutinin; Henion et al, Vaccine, 15:1174-1182 (1997); gp120; Abdel-Motal et al., J. Virology, 80:6943-6951 (2006); and on cancer cells; Unfer et al., Cancer Res., 63:987-993 (2003).

SUMMARY OF THE INVENTION

Accordingly, one aim of the present invention is the development of further protein expression systems for yeasts and filamentous fungi, such as *Pichia pastoris*, based on improved vectors and host cell lines for the production of effective protein-based vaccines with increased immunogenicity.

The present invention provides improved methods and materials for the production of such vaccines using genetically engineered host strains of yeast and filamentous fungi. The host strains have been genetically modified for the production of proteins having human like N-glycosylation.

The present invention can be used to improve the current state of the art of protein-based vaccines. A glycosylated protein vaccine produced in the genetically engineered strains described herein can be expected to elicit an elevated immune response through improved antigen presentation compared to a vaccine with terminal β-1,4 galactose, terminal sialic acid, or terminal mannose. This technology is applicable to any number of vaccines that can be developed as recombinant protein-based molecules.

Recent developments allow the production of fully humanized therapeutics in lower eukaryotic host organisms, yeast and filamentous fungi, such as *Pichia pastoris*. Gerngross, U.S. Pat. No. 7,029,872, the disclosure of which is hereby incorporated by reference. The present inventors have developed further modifications to produce host organisms which can be used for commercial scale production of vaccines in which the protein produced contains at least one terminal α-1,3-galactose glycoform.

The present inventors have found that vaccine glycoproteins having terminal α-1,3-galactose can be obtained from recombinant host cells by modifying the glycosylation machinery present in the cells. The inventors surprisingly found that beneficial results were obtained by replacing the host cell's endogenous genes encoding glycosylation proteins, with heterologous genes encoding glycosylation enzymes such that N-glycans having terminal α-1,3-galactose residues are present on the antigenic glycoprotein produced by the host cell.

In preferred embodiments of the present invention, one can modify the genome of lower eukaryotic cells, such as yeast and filamentous fungi, for example, *Pichia pastoris*. The resulting transformed lower eukaryotic host cell is able to produce antigenic vaccine glycoproteins with terminal α-1,3-galactose residues on a sufficiently high proportion of N-glycans such that the antigenicity/immunogenicity of the resulting vaccine glycoproteins is improved. The present invention has additional advantages in that lower eukaryotic host cells, such as *Pichia pastoris*, are able to produce vaccine glycoproteins at high yield, with the predominant species of glycoprotein having terminal α-1,3-galactose residues with improved antigenicity compared to production of the vaccine protein in lower eukaryotic host cells retaining their endogenous glycosylation machinery or other standard protein production hosts such as insect cells or mammalian cell lines like CHO or NS0.

In a particular embodiment, a codon optimized (for *P. Pastoris*) open reading frame encoding an *S. scrofa* alpha-1,3-galactosyl transferase (Genebank: P50127) is engineered into a *P. pastoris* yeast strain. In a preferred embodiment, the enzyme is engineered to be specifically localized to the yeast Golgi to optimize its activity. Particular targeting sequences can be chosen by screening fusion protein constructs for the most active fusion proteins. In an exemplified embodiment, the *S. scrofa* alpha-1,3-galactosyl transferase is fused to a ScMnn2p transmembrane Golgi targeting localization domain.

Embodiments of this invention include a lower eukaryotic host cell, more preferably a yeast or filamentous fungal host cell, which has been engineered to produce glycoproteins having a predominant N-glycan comprising a terminal α-galactosyl epitope.

Embodiments of this invention include a lower eukaryotic host cell, more preferably a yeast or filamentous fungal host cell, wherein the host cell produces glycoproteins having an N-glycan comprising a terminal α-galactosyl epitope, wherein the predominant N-glycan is selected from the group consisting of (α-Gal)(β-Gal)GlcNAcMan5GlcNAc2; (α-Gal)(β-Gal)2GlcNAc2Man3GlcNAc2; and (α-Gal)2(β-Gal)2GlcNAc2Man3GlcNAc2.

Embodiments of this invention include a lower eukaryotic host cell, more preferably a yeast or filamentous fungal host cell, wherein the host cell has been engineered to produce a vaccine protein.

Embodiments of this invention include a lower eukaryotic host cell, more preferably a yeast or filamentous fungal host cell, wherein the vaccine glycoprotein is derived from an anti-viral vaccine protein, an anti-bacterial vaccine protein or an anti-cancer vaccine protein.

Embodiments of this invention include a lower eukaryotic host cell, more preferably a yeast or filamentous fungal host cell, wherein the anti-viral vaccine protein is from an influenza virus. More preferably, the influenza proteins are hemagglutinin (HA) or neuraminidase (NA) glycoproteins.

Embodiments of this invention include a lower eukaryotic host cell, more preferably a yeast or filamentous fungal host cell, wherein the anti-viral vaccine protein is from a herpes simplex virus. More preferably, herpes envelope glycoproteins gB, gC, and gD are used.

Embodiments of this invention include a lower eukaryotic host cell, more preferably a yeast or filamentous fungal host cell, wherein the anti-viral vaccine protein is from respiratory syncytial virus (RSV). More preferably viral vaccine glycoproteins are selected from the group consisting of RSV hemagglutinin glycoprotein (H); and fusion glycoprotein F.

Embodiments of this invention include a lower eukaryotic host cell, more preferably a yeast or filamentous fungal host cell, wherein the anti-bacterial vaccine glycoprotein is derived from a bacterial vaccine protein. More preferably the bacterial vaccine protein is an integral membrane protein, or is an outer membrane protein, or is an outer surface protein, or is from *Mycobacterium*, or is from *Salmonella*, or is from *Borrelia*, or is from *Haemophilus*.

Embodiments of this invention include a lower eukaryotic host cell, more preferably a yeast or filamentous fungal host cell, wherein the anti-cancer vaccine glycoprotein is derived from an epitopic peptide derived from a cancer cell such as a Her-2 epitope, a neu epitope or a prostate stem cell antigen (PSCA) epitope.

BRIEF DESCRIPTION OF THE FIGURES

FIGS. 6A & 6B. Comparison of α-1,3-galactosyl transferase proteins reveals a high degree of similarity. *Bos Taurus* (SEQ ID NO:8), *Sus scrofa* (SEQ ID NO: 10), *Mus musculus* (SEQ ID NO: 11), *Canis familiaris* (SEQ ID N0:9) α-Gal1 protein sequences were compared by performing ClustalV analysis using Lasergene (DNAstar, Madison, WI).

DESCRIPTION OF THE SEQUENCES

Figure 1:
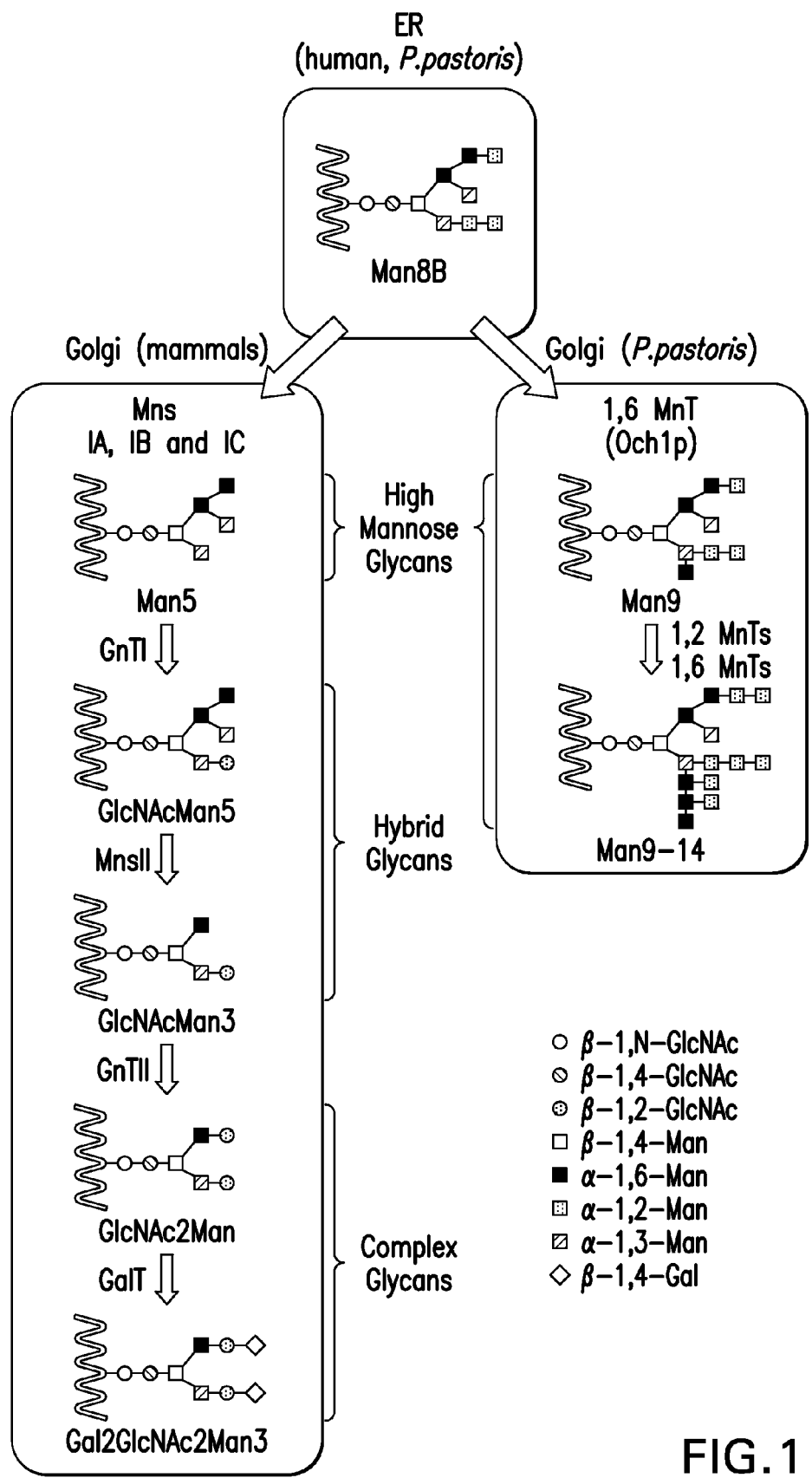
FIG. 1. A comparison of the N-glycosylation machinery between yeast and mammals. Both produce a Man$_8$GlcNAc$_2$ precursor following protein folding and ER maturation. N-glycosylation pathways differ in the Golgi with mammals trimming mannose and adding additional sugars such as GlcNAc and galactose to produce complex N-glycans. In contrast, yeast add additional mannose with various linkages, including an outer chain, which can be comprised of dozens of mannose residues.
Figure 2:
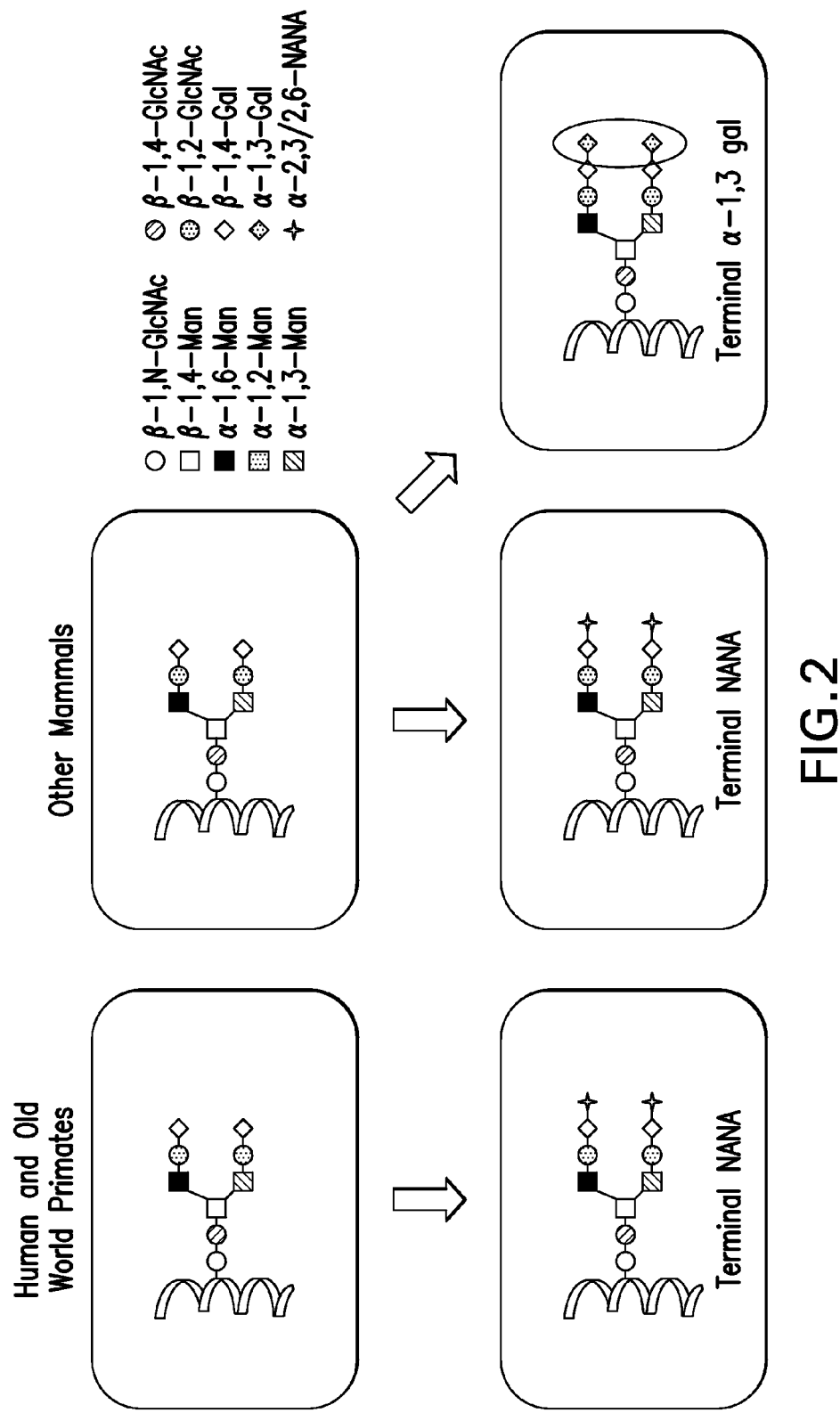
FIG. 2. Comparison of the terminal sugars found on N-glycans between humans and most other mammals. Most mammals exhibit a minor percentage of terminal α-1,3-linked galactose, a structure completely lacking from the N-glycans of humans.

SEQUENCE ID NOs: 1 and 2 are nucleotide sequences of RCD446 and RCD447, primers for the cloning of murine α-1,3-galactosyl transferase lacking the putative transmembrane Golgi localization domain (MmαGalT).

```
RCD446 Primer
                            Sequence ID NO. 1
TTGGCGCGCCAACAGCCCAGACGGCTCTTTCTTG RCD447 Primer
                            Sequence ID NO. 2
GGTTAATTAATCAGACATTATTTCTAACCAAATT
```

SEQUENCE ID NO: 3 is an amino acid sequence of the ectodomain (i.e. lacking the C-terminal transmembrane domain) of type H3 HA protein from Influenza A (Hong Kong).

```
                            Sequence ID NO. 3
QDLPGNDNSTATLCLGHHAVPNGTLVKTITDDQIEVTNATELVQ

SSSTGKICNNPHRILDGIDCTLIDALLGDPHCDVFQNETWDLFV

ERSKAFSNCYPYDVPDYASLRSLVASSGTLEFITEGFTWTGVTQ

NGGSNACKRGPGSGFFSRLNWLTKSGSTYPVLNVTMPNNDNFDK

LYIWGVHHPSTNQEQTSLYVQASGRVTVSTRRSQQTIIPNIGSR

PWVRGLSSRISIYWTIVKPGDVLVINSNGNLIAPRGYFKMRTGK

SSIMRSDAPIDTCISECITPNGSIPNDKPFQNVNKITYGACPKY

VKQNTLKLATGMRNVPEKQTRGLFGAIAGFIENGWEGMIDGWYG

FRHQNSEGTGQAADLKSTQAAIDQINGKLNRVIEKTNEKFHQIE

KEFSEVEGRIQDLEKYVEDTKIDLWSYNAELLVALENQHTIDLT

DSEMNKLFEKTRRQLRENAEDMGNGCFKIYHKCDNACIESIRNG

TYDHDVYRDEALNNRFQIKGVELKSGYKDWILWISFAISCFLLC

VVLLGFIMWACQRGNIRCNICIGGGHHHHHHHH
```

SEQUENCE ID NO: 4 is an amino acid sequence of nucleotide the ectodomain (i.e. lacking the C-terminal transmembrane domain) of type H1 HA protein from Influenza A (A/South Carolina/1/18).

```
                                Sequence ID NO. 4
DTICIGYHANNSTDTVDTVLEKNVTVTHSVNLLEDSHNGKLCKL

KGIAPLQLGKCNIAGWLLGNPECDLLLTASSWSYIVETSNSENG

TCYPGDFIDYEELREQLSSVSSFEKFEIFPKTSSWPNHETTKGV

TAACSYAGASSFYRNLLWLTKKGSSYPKLSKSYVNNKGKEVLVL

WGVHHPPTGTDQQSLYQNADAYVSVGSSKYNRRFTPEIAARPKV

RDQAGRMNYYWTLLEPGDTITFEATGNLIAPWYAFALNRGSGSG

IITSDAPVHDCNTKCQTPHGAINSSLPFQNIHPVTIGECPKYVR

STKLRMATGLRNIPSIQSRGLFGAIAGFIEGGWTGMIDGWYGYH

HQNEQGSGYAADQKSTQNAIDGITNKVNSVIEKMNTQFTAVGKE

FNNLERRIENLNKKVDDGFLDIWTYNAELLVLLENERTLDFHDS

NVRNLYEKVKSQLKNNAKEIGNGCFEFYHKCDDACMESVRNGTY

DYPKYSEESKLNREEIDGVKLESMGVYQIGGGHHHHHHHHH
```

SEQUENCE ID NOS: 5 and 6 are amino acid sequences of two different versions of the HSV-2 G strain gD protein ectodomain.

```
HSV-2 G strain gD 339 protein ectodomain
                                Sequence ID NO. 5
KYALADPSLKMADPNRFRGKNLPVLDQLTDPPGVKRVYHIQPSL

EDPFQPPSIPITVYYAVLERACRSVLLHAPSEAPQIVRGASDEA

RKHTYNLTIAWYRMGDNCAIPITVMEYTECPYNKSLGVCPIRTQ

PRWSYYDSFSAVSEDNLGFLMHAPAFETAGTYLRLVKINDWTEI

TQFILEHRARASCKYALPLRIPPAACLTSKAYQQGVTVDSIGML

PRFIPENQRTVALYSLKIAGWHGPKPPYTSTLLPPELSDTTNAT

QPELVPEDPEDSALLEDPAGTVSSQIPPNWHIPSIQDVAPHHAP

AAPSNPGGGHHHHHHHH

HSV-2 G strain gD 306NQ protein ectodomain
                                Sequence ID NO. 6
KYALADPSLKMADPNRFRGKNLPVLDQLTDPPGVKRVYHIQPSL

EDPFQPPSIPITVYYAVLERACRSVLLHAPSEAPQIVRGASDEA

RKHTYNLTIAWYRMGDNCAIPITVMEYTECPYNKSLGVCPIRTQ

PRWSYYDSFSAVSEDNLGFLMHAPAFETAGTYLRLVKINDWTEI

TQFILEHRARASCKYALPLRIPPAACLTSKAYQQGVTVDSIGML

PRFIPENQRTVALYSLKIAGWHGPKPPYTSTLLPPELSDTTNAT

QPELVPEDPEDSALLEDNQGGHHHHHHHH
```

SEQUENCE ID NO: 7 is an amino acid sequence of the HSV-2 G strain gC protein ectodomain.

```
HSV-2 G strain gC protein ectodomain
                                Sequence ID NO. 7
LANASPGRTITVGPRGNASNAAPSASPRNASAPRTTPTPPQPRK

ATKSKASTAKPAPPPKTGPPKTSSEPVRCNRHDPLARYGSRVQI

RCRFPNSTRTEFRLQIWRYATATDAEIGTAPSLEEVMVNVSAPP

GGQLVYDSAPNRTDPHVIWAEGAGPGASPRLYSVVGPLGRQRLI

IEELTLETQGMYYWVWGRTDRPSAYGTWVRVRVFRPPSLTIHPH

AVLEGQPFKATCTAATYYPGNRAEFVWFEDGRRVFDPAQIHTQT

QENPDGFSTVSTVTSAAVGGQGPPRTFTCQLTWHRDSVSFSRRN

ASGTASVLPRPTITMEFTGDHAVCTAGCVPEGVTFAWFLGDDSS

PAEKVAVASQTSCGRPGTATIRSTLPVSYEQTEYICRLAGYPDG

IPVLEHHGSHQPPPRDPTERQVIRAIEGRGGGHHHHHHHHH
```

DETAILED DESCRIPTION OF THE INVENTION

Unless otherwise defined herein, scientific and technical terms and phrases used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques used to make basic genetic constructs of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual,* 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; Handbook of Biochemistry: Section A Proteins, Vol I, CRC Press (1976); *Handbook of Biochemistry: Section A Proteins*, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

As used herein, the terms "N-glycan" and "glycoform" are used interchangeably and refer to an N-linked oligosaccharide, e.g., an oligosaccharide that is attached by an asparagine-N-acetylglucosamine linkage between and N-acetylglucosamine residue of the oligosaccharide and an asparagine residue of a polypeptide. The predominant sugars found on glycoproteins are glucose (Glc), galactose (Gal), mannose (Man), fucose (Fuc), N-acetylgalactosamine (GalNAc), N-acetylglucosamine (GlcNAc) and sialic acid (e.g., N-acetyl-neuraminic acid (NANA) and N-glycolyl-neuraminic acid (NGNA)). The processing of the sugar groups occurs co-translationally in the lumen of the ER and continues in the Golgi apparatus for N-linked glycoproteins.

N-glycans have a common pentasaccharide core of $Man_3GlcNAc_2$. N-glycans differ with respect to the number of branches (antennae) comprising peripheral sugars (e.g., GlcNAc, galactose, fucose and sialic acid) that are added to the Man3GlcNAc2 ("Man3") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the α-1,3 mannose arm and at least one GlcNAc attached to the α-1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). "α-Gal" refers to an α-1,3-linked galactose and "β-Gal" refers to a β-1,4-linked galactose. Complex N-glycans may also have intrachain substitutions comprising "bisecting" GlcNAc and core fucose. Complex N-glycans may also have multiple antennae on the "trimannose core," often referred to as "multiple antennary glycans." A "hybrid" N-glycan has at least one β-GlcNAc attached to the nonreducing end of the α-1,3 mannose arm of the trimannose core and zero or more mannoses on the α-1,6 mannose arm of the trimannose core. The various N-glycans are also referred to as "glycoforms."

Abbreviations used herein are of common usage in the art, see, e.g., abbreviations of sugars, above. Other common abbreviations include "PNGase", or "glycanase" which all refer to peptide N-glycosidase F (EC 3.2.2.18).

The term "marker sequence" or "marker gene" refers to a nucleic acid sequence capable of expressing an activity that allows either positive or negative selection for the presence or absence of the sequence within a host cell. For example, the P. pastoris URA5 gene is a marker gene because its presence can be selected for by the ability of cells containing the gene to grow in the absence of uracil. Its presence can also be selected against by the inability of cells containing the gene to grow in the presence of 5-FOA. Marker sequences or genes do not necessarily need to display both positive and negative selectability. Non-limiting examples of marker sequences or genes from P. pastoris include ADE1, ARG4, HIS4 and URA3. For antibiotic resistance marker genes, kanamycin, neomycin, geneticin (or G418), paromomycin and hygromycin resistance genes are commonly used to allow for growth in the presence of these antibiotics.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences, which are necessary to affect the expression of coding sequences to which they are operatively linked. Expression control sequences are sequences that control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "eukaryotic" refers to a nucleated cell or organism, and includes insect cells, plant cells, mammalian cells, animal cells and lower eukaryotic cells.

The term "lower eukaryotic cells" includes yeast, fungi, collar-flagellates, microsporidia, alveolates (e.g., dinoflagellates), stramenopiles (e.g, brown algae, protozoa), rhodophyta (e.g., red algae), plants (e.g., green algae, plant cells, moss) and other protists. Yeast and filamentous fungi include, but are not limited to: *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa. Pichia sp.,* any *Saccharomyces* sp., *Hansenula polymorpha*, any *Kluyveromyces* sp., *Candida albicans*, any *Aspergillus* sp., *Trichoderma reesei, Chrysosporium lucknowense*, any *Fusarium* sp. and *Neurospora crassa*.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof as indicated by the context of use. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long. A fragment may comprise a domain with a distinctive activity.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}$I, $^{32}$P, $^{35}$S, and $^3$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "chimeric gene" or "chimeric nucleotide sequences" refers to a nucleotide sequence comprising a nucleotide sequence or fragment coupled to one or more heterologous nucleotide sequences. Chimeric sequences are useful for the expression of fusion proteins. Chimeric genes or chimeric nucleotide sequences may also comprise one or more fragments or domains which are heterologous to the intended host cell, and which may have beneficial properties for the production of heterologous recombinant proteins. Generally, a chimeric nucleotide sequence comprises at least 30 contiguous nucleotides from a gene, more preferably at least 60 or 90 or more nucleotides. Chimeric nucleotide sequences which have at least one fragment or domain which is heterologous to the intended host cell, but which is homologous to the intended recombinant protein, have particular utility in the present invention. For example, a chimeric gene intended for use in an expression system using *P. pastoris* host cells to express recombinant human glycoproteins will preferably have at least one fragment or domain which is of human origin, while the remainder of the chimeric gene will preferably be of *P. pastoris* origin.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions also include larger polypeptides, or even entire proteins, such as the green fluorescent protein ("GFP") chromophore-containing proteins having particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, the twenty conventional amino acids and their abbreviations follow conventional usage. See *Immunology—A Synthesis* (Golub and Gren eds., Sinauer Associates, Sunderland, Mass., 2$^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule.

As used herein, the term "molecule" means any compound, including, but not limited to, a small molecule, peptide, protein, sugar, nucleotide, nucleic acid, lipid, etc., and such a compound can be natural or synthetic.

As used herein, the term "comprise" or variations such as "comprises" or "comprising", will be understood to imply the inclusion of a stated integer or group of integers but not the exclusion of any other integer or group of integers.

As used herein, the term "predominantly" or variations such as "the predominant" or "which is predominant" will be understood to mean the glycan species that has the highest mole percent (%) of total N-glycans that can be identified after the glycoprotein has been treated with PNGase and the released glycans are analyzed by mass spectroscopy, for example, MALDI-TOF MS. In other words, the term "predominant" is defined as an individual entity, such as a specific glycoform, that is present in greater mole percent than any other individual entity. For example, if a composition consists of species A in 40 mole percent, species B in 35 mole percent and species C in 25 mole percent, species A is "predominant" the composition comprises "predominantly" species A.

As used herein, the term "vaccine protein" or "vaccine glycoprotein" will be understood to mean that the "vaccine protein" or "vaccine glycoprotein" is intended to be utilized as a vaccine, which may be administrable to humans, and which is intended to elicit an immune response to the protein or glycoprotein used as a the "vaccine protein" or "vaccine glycoprotein." The vaccine protein or vaccine glycoprotein may comprise a full-length native protein or glycoprotein, or it may comprise one or more domains isolated from a native protein or glycoprotein. The vaccine protein or vaccine glycoprotein may be utilized in a vaccine together with other vaccine proteins or vaccine glycoproteins, as well as in formulations comprising additional active agents and/or pharmaceutical carriers. The term "vaccine protein" or "vaccine glycoprotein" may also be used interchangeably with the term "target protein" or "target glycoprotein."

As used herein the term "epitope" refers to the portion of an antigen that is capable of eliciting an immune response or capable of being recognized by an antibody. Epitopes frequently consist of a conjunction of multiple amino acids, carbohydrate moiety(ies) or both. Epitopes that are referred to as linear frequently do not depend on proper folding of a protein. Epitopes that depend on the proper folding of a protein are referred to as conformational because the epitope is only present when the protein is in its properly folded conformation.

As used herein, the term "α-galactosyl epitope" means a terminal galactose residue linked α-1,3 to a second galactose residue, the second galactose residue being linked β-1,4 to an N-acetyl glucosamine residue. Examples of glycans with an α-galactosyl epitope include the following branched glycan structures (α-Gal)(β-Gal)GlcNAcMan5GlcNAc2; (α-Gal)(β-Gal)2GlcNAc2Man3GlcNAc2; and (α-Gal)2(β-Gal)2GlcNAc2Man3GlcNAc2. See also GS5.7, GS5.8 and GS5.9 in FIG. 3. As used herein the term "adjuvant" refers to a compound or substance capable of increasing the immunogenic response to a vaccine or vaccine protein without having any specific antigenic effect itself. Adjuvants can include bacterial lipopolysaccharide, liposomes, aluminum salts and oils.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting in any manner.

I. General

The invention provides methods and materials for the expression of vaccine glycoproteins having α-linked galactose from recombinant host cells, which recombinant host cells have been transformed with vectors encoding vaccine proteins. The vaccine glycoproteins result in improved quality of the recombinant glycoprotein produced from the host cell, particularly increased immune response obtained from vaccine glycoproteins produced in the recombinant host cells transformed with these vectors.

Although the methods are exemplified with respect to expression in lower eukaryotic organisms, particularly yeast, they can also be practiced in higher eukaryotic organisms and bacteria. The methods involve transforming host cells with a nucleic acid molecule which encodes an improved vaccine protein, especially a vaccine glycoprotein, and thereby, when the host cells are transformed with an expression vector encoding a secreted glycoprotein, the α-linked galactose may contributes to improved quality of the recombinant secreted glycoprotein, particularly, increased immune response to the produced antigenic glycoprotein.

Accordingly, in preferred embodiments, the methods of the present invention may be used in recombinant expression systems using cells which have been engineered for production of the improved secreted vaccine glycoproteins.

II. Expression of Vaccine Proteins

Nucleic Acid Encoding the Vaccine Protein or Glycoprotein

Glycoproteins described above are encoded by nucleic acids. The nucleic acids can be DNA or RNA, typically DNA. The nucleic acid encoding the glycoprotein is operably linked to regulatory sequences that allow expression and secretion of the glycoprotein. Such regulatory sequences include a promoter and optionally an enhancer upstream, or 5', to the nucleic acid encoding the protein and a transcription termination site 3' or downstream from the nucleic acid encoding the glycoprotein. The glycoprotein can be a fusion protein. For secreted glycoproteins, the nucleic acid typically includes a leader sequence encoding a leader or signal peptide. The leader or signal peptide is responsible for targeting the protein to the appropriate cellular compartments of the secretory pathway for glycosylation and secretion, typically the endoplasmic reticulum or the Golgi apparatus. The nucleic acid also typically encodes a 5' untranslated region having a ribosome binding site and a 3' untranslated region. The nucleic acid is often a component of a vector replicable in cells in which the glycoprotein is expressed. The vector can also contain a marker to allow recognition of transformed cells. However, some cell types, particularly yeast, can be successfully transformed with a nucleic acid lacking extraneous vector sequences.

Nucleic acids encoding desired glycoproteins can be obtained from several sources. cDNA sequences can be amplified from cell lines known to express the glycoprotein using primers to conserved regions (see, e.g., Marks et al., J. Mol. Biol. 581-596 (1991)). Nucleic acids can also be synthesized de novo based on sequences in the scientific literature. Nucleic acids can also be synthesized by extension of overlapping oligonucleotides spanning a desired sequence (see, e.g., Caldas et al., Protein Engineering, 13, 353-360 (2000)). If desired, nucleic acid sequences can be codon-optimized according to preferred codon usage tables to improve expression in the host cell of the invention (see, e.g., Chang et al., J. Agric. Food Chem. 54:815-822 (2006). Production of active glycoproteins may require proper folding of the protein when it is produced and secreted by the cells. However such folding may not be essential in order to use the protein as a vaccine protein, for example, when the epitopes of interest are linear. The presence of terminal alpha-1,3-galactose residues may be required for immunogenicity of a vaccine glycoprotein, or may enhance the immunogenicity of the vaccine glycoproteins being produced.

III. Viral and Other Vaccine Targets

Vaccine targets which may be appropriate for the present invention include those to which an antigenic response may be boosted by attachment of an alpha-gal moiety to the end of an antigen. In preferred embodiments, the vaccine protein will comprise a peptide or protein derived from the target. The target is preferably a disease vector, such as a virus, fungus, bacteria, or other microbe. In other embodiments, the target may be a particular type of cell, such as a cancer cell, which expresses a known epitopic peptide which can be used as the target protein. For example, preferred epitopic peptides may be selected from the group consisting of a Her-2 epitope, a neu epitope or a prostate stem cell antigen (PSCA) epitope.

Preferred viral targets include those viruses known to cause diseases in humans and/or animals, such as influenza viruses (e.g., influenza A, B or HN51); herpes simplex viruses (HSV, e.g., HSV-1 and HSV-2, which is associated with genital herpes); hepatitis viruses, respiratory syncytial virus (RSV), parainfluenza viruses (PIV, e.g., PIV-type III), human papillomaviruses (HPV, e.g., HPV-16, which may be associated with cervical cancer), Epstein-Barr virus, adenoviruses, human immunodeficiency viruses (HIV, which is associated with AIDS), and human cytomegalovirus (CMV), paramoxyviruses (such as those associated with mumps and measles), poxviruses, Reoviridae, (including rotaviruses, reovirus and Colorado Tick Fever virus) and polioviruses.

The preferred target proteins for viruses include capsid proteins, surface coat proteins, structural proteins, and other proteins which may be accessible to the immune system, especially those proteins which are naturally glycosylated. One or more additional glycosylation sites may be engineered into the DNA sequence encoding the target protein. Where there is no natural glycosylation site, one or more artificial glycosylation sites may be engineered into a DNA sequence encoding the target protein. DNA sequences encoding the target protein may be cloned or synthesized, and may be optimized for expression in the host cells of the present invention.

The vaccine protein useful in the present invention may comprise all or fragments of one or more of the following viral proteins. One skilled in the art may locate or identify additional suitable viral proteins by reference to the continually expanding viral genomic databases, such as the website of the International Committee on Taxonomy of Viruses: The Universal Virus Database, version 3.

In preferred embodiments, one or more viral proteins or glycoproteins may be used together as part of a compound vaccine. The compound vaccine may comprise multiple vaccine proteins from the same target virus, as well as multiple vaccine proteins from distinct target viruses. The following are non-limiting examples of the target viruses and viral proteins which may serve as the vaccine protein in the present invention:

Influenza Viruses (hemagglutinin (HA) glycoprotein; neuraminidase (NA) glycoprotein; matrix protein; M1 protein; M2 protein; M3 protein; nucleoprotein (NP) peptide; PA protein; PB1 protein and PB2 protein; Rev protein. See McCauley and Mahy, Biochem. J., 211:281-294 (1983); Lamb et al., Proc Natl Acad Sci USA., 78:4170-4174 (1981)).

Herpesvirus (including Herpes Simplex Viruses and Cytomegaloviruses): Envelope glycoproteins: glycoprotein B (also called VP7); glycoprotein C/VP7.5; glycoprotein D/VP17/18; envelope glycoprotein E; envelope glycoprotein G; envelope glycoprotein H; envelope glycoprotein I; envelope glycoprotein J; envelope glycoprotein K; envelope glycoprotein L; envelope glycoprotein M; envelope glycoprotein N; small capsid protein; tegument proteins: VP11/12; VP13/14; VP22; and VP-5/ICP5; VP19c; VP23; VP26; ICP1-2; ICP35; ICP47. See, Roizman, Proc Natl Acad Sci USA 93: 11307-11312 (1996); Whitley and Roizman, J. Clin. Invest. 110(2): 145-151 (2002); Dunn et al., Proc Natl Acad Sci USA, 100:14223-14228 (2003). Herpes viruses also include Varicella Zoster (cause of chicken pox); and Epstein-Barr virus.

Flavivirus (which can include Dengue virus; West Nile virus; hepatitis viruses; and GB viruses); Dengue: Protein C; Protein M; Protein E. See, Chambers et al, Annual Review of Microbiology; 44: 649-688 (1990). Hepatitis viruses: (including GB Virus) surface antigens, such as HBsAg; p17e/HBeAg; HBe1; HBe2; p21c/HBcAg; P39/GP42; p24/GP27; GP33/GP36; preS1; pre-S2; S protein; p74 (NS3); p68 (NS5B); p20 (core protein); HDAg-p24; HDAg-p27. See Sells et al., PNAS USA 84:1005-1009 (1987); Heermann et al., J. Virology 52:396-402(1984); Svitkin et al., J. Virology; 79:6868-6881 (2005); Salfeld et al., J. Virology 63:798-808 (1989); Grottola et al., Liver Transpl. 8:443-448 (2002); Casey et al., PNAS, USA; 90:9016-9020 (1993). GB Virus: envelope proteins: E1 glycoprotein; E2. See: Muerhoff et al., J. Virology 71:6501-6508; Bukh et al., WO2000/075337.

Paramyxoviridae/Paramoxyvirus; including: Parainfluenzaviruses (PIV), such as human PIV-1 (Respirovirus) and human PIV-2 and -4 (Rubulavirus); Pneumoviruses such as respiratory synctial virus (RSV); Morbilliviruses, such as Mumps Virus and Measles Virus; Henipavirus, such as Hendravirus and Nipahvirus; and Metapneumoviruses. Typically, the genome includes genes encoding both a nucleocapsid (N) protein; and a nucleocapsid phosphoprotein (P), both of which may serve as the viral vaccine protein. See, Collins, U.S. Pat. No. 6,264,957; certain of the paramyxoviruses, also contain a neuraminidase (NA) protein which can serve as the viral vaccine protein in the present invention. The virus frequently also carries hemagglutinin (H) and fusion (F) glycoproteins on its surface, which can comprise viral vaccine proteins.

Human papillomaviruses (HPV, e.g., HPV-16, which may be associated with cervical cancer), capsid proteins encoded by L1 and L2; E7 antigenic peptide. See Carter et al., J. Virol. 80: 4664-72 (2006); Pastrana et al., Virology 337: 365-72 (2005).

Filoviruses (including Ebola virus). VP30; VP35; Polymerase L protein; VP40; VP24; and GP/SGP glycoprotein. See Folks, Nature Medicine 4:16-17 (1998); and Feldmann, Virus Research 24:1-19 (1992).

Adenoviruses: Protein II (Hexon monomer S); Capsid Proteins S (III) and IIIa (Penton Base Proteins); Fiber Protein IV; Proteins VI, VIII, and IX (Hexon Minor Polypeptides). See, Russell, J. General Virology 81:2573-2604 (2000); Roulston et al, Annu Rev Microbiol 53:577-628 (1999); and Yewdell and Bennink; Annu Rev Cell Dev Biol. 15:579-606 (1999).

Lentiviruses, such as Human immunodeficiency viruses (associated with acquired immunodeficiency syndrome (AIDS)): Envelope glycoproteins (GP120 and GP41); viral capsid protein (p24); Nucleocapsid proteins (p6 and p'7); and matrix protein (p17); HIV regulatory proteins (Tat, Rev, Nef). See, Wain-Hobson, S., 1989. HIV genome variability in vivo. AIDS 3: supp 1; 13-9 (1989); and Ratner et al., Nature 313:277-84 (1985).

Bunyaviridae (including Hantavirus) envelope glycoproteins (glycoproteins GP1; GP2); nucleocapsid proteins (protein N). See Schmaljohn et al., J. Gen. Virol. 69:1949-1955 (1988).

Nidoviruses (Coronaviruses and Arteriviruses): (including viruses associated with severe acute respiratory syndrome (SARS)). S (spike glycoprotein); E (envelope protein); M (Membrane glycoprotein); and HE (Haemagglutinin-esterase); N (phosphoprotein). See, Pyrc et al., Virology J. (2004).

Reoviridae, (including Rotaviruses, reovirus and Colorado Tick Fever virus): σ1, σ2, and σ3; μ1c; VP1, VP2, VP3, VP4, VP6 and VP7). See Joklik, Microbiological Reviews, 45:483-501 (1981).

Picornaviridae, including Polioviruses: Viral capsid proteins: VP1, VP2; VP3 and VP4. See, Koch and Koch, The Molecular Biology of Poliovirus. Springer-Verlag/Wein (NY, 1985).

IV. Bacterial and Other Vaccine Targets

Preferred bacterial targets in the present invention include those known to cause diseases in humans and/or animals, such as *Mycobacterium* (Tuberculosis; leprosy; chronic infections); *Haemophilus influenzae* (Respiratory infections; meningitis; conjunctivitis; chancroid); *Mycoplasma* (Atypical pneumonia; urogenital infections); *Bacillus* (Anthrax; food poisoning); *Salmonella* (Typhoid fever; enteritis; food poisoning); *Clostridium* (Tetanus; botulism; gas gangrene; bacteremia); *Treponema* (syphilis); *Borrelia* (Relapsing fever; Lyme disease); *Ureaplasma* (Opportunistic urogenital infections); *Staphylococcus* (Skin abscesses; opportunistic infections); *Streptococcus* (Strep throat and other respiratory infections; skin and other abscesses; puerperal fever; opportunistic infections); *Leptospira* (Leptospirosis); *Campylobacter* (Urogenital/digestive tract infections); *Heliobacter* (Peptic ulcers); *Pseudomonas* (Urinary tract infections; burns; wounds); *Legionella* (Pneumonia; respiratory infections); *Neisseria* (Gonorrhea; meningitis; nasopharyngeal infections); *Moraxella* (Conjunctivitis); *Brucella* (Brucellosis); *Bordetella* (Whooping cough); *Francisella* (Tularemia); *Escherichia* (Opportunistic infections of colon and other sites); *Shigella* (Bacterial dysentery); *Klebsiella* (Respiratory and urinary tract infections); *Enterobacter* (Opportunistic infections); *Serratia* (Opportunistic infections); *Proteus* (Urinary tract infections); *Providencia* (Wound and burn infections; urinary tract infections); *Morganella* (Summer diarrhea; opportunistic infections); *Yersinia* (Plague; mesenteric lymphadenitis; septicemia); *Vibrio* (Cholera; acute gastroenteritis); *Pasteurella* (Infections associated with cat- and dog-bite wounds); *Calymmatobacterium* (Granuloma inguinale); *Gardnerella* (Vaginitis); Eikenella (Wound infections); *Streptobacillus* (Infections associated with rat-bites); *Bacteroides*/fusobacterium (Oral, digestive, respiratory and urogenital infections; wounds and abscesses); *Veillonella* (oral microbiota and abscesses); *Rickettsia* (Typhus; Rocky mountain spotted fever; rickettsialpox); *Rochalimaea* (Trench fever); *Coxiella* (Q fever); *Bartonella* (*Oroya fever*); *Chlamydia* (Trachoma; inclusion conjunctivitis; non-gonococcal urethritis; parrot fever); Peptococcus (Postpartum septicemia; visceral lesions); *Peptostreptococcus* (Puerperal fever; pyogenic infections); Laactobacillus (Microflora of digestive tract and vagina); *Listeria* (Listeriosis); *Erysipolothrix* (Erysipeloid); *Corynebacterium* (Diphtheria and skin opportunists); *Propionibacterium* (Wound infections and diseases); *Eubacterium* (Oral and other infections); *Actinomyces* (Actinomycoses); *Nocardia* (Nocardiosis; mycetoma; abscesses); and *Dermatophilus* (Skin lesions).

The preferred target proteins for bacteria include membrane proteins, structural proteins, and other proteins which may be accessible to the immune system, especially those proteins which are naturally glycosylated. One or more additional glycosylation sites may be engineered into the DNA sequence encoding the target protein. Where there is no natural glycosylation site, one or more artificial glycosylation sites may be engineered into a DNA sequence encoding the target protein. The target may also comprise a peptide fused to a polysaccharide or lipid, wherein the polysaccharide or lipid may optimally be derived from a polysaccharide or lipid which naturally surrounds or encapsulates the target bacteria. DNA sequences encoding the target protein may be cloned or synthesized, and may be optimized for expression in the host cells of the present invention.

The vaccine protein useful in the present invention may comprise all or fragments of the target bacterial protein or proteins. One skilled in the art may locate or identify additional suitable bacterial proteins by reference to the continually expanding bacterial genomic databases, such as those available at the website of the Sanger Center In preferred embodiments, one or more bacterial proteins or glycoproteins may be used together as part of a compound vaccine. The compound vaccine may comprise multiple vaccine proteins from the same target bacterium, as well as multiple vaccine proteins from distinct target bacteria, as well as vaccine proteins from target viruses or other epitopic peptides, such as epitopes to cancer cells. The following are non-limiting examples of target bacteria and bacterial proteins, which may be used as the vaccine protein in the present invention.

*Salmonella* (Typhoid fever; enteritis; food poisoning). Envelope proteins (envA; envD; envZ/ompB/tppA/tppB) Outer membrane proteins (ompA; ompC; ompD; ompF; ompH; ompR; pefC; pss; rck; spvA; tctA; tctB); Outer membrane porin protein (nmpC); Outer membrane protease E (pgtE); Outer membrane phospholipase A (p1dA); Phosphate limitation-inducible outer membrane pore protein (phoE); Spermidine and putrecine transporter (potA); membrane-bound acyl amino acid esterase (apeE); Membrane-bound sensor (arcB); membrane-bound attachment site (atdA). See: Wu et al, J. Bacteriol. 187:4720-4727 (2005); see also: www.salmonell.org/genomics/.

*Mycobacterium* (Tuberculosis; leprosy; chronic infections) Integral membrane proteins (amt; arsA; arsB1; arsB2; arsC; betP; chaA; cysT; cysW; dppB; dppC; drrB; drrC). See Camus et al., Microbiology 148:2967-2973 (2002; Cole et al. Nature 393:537-544 (1998).

*Haemophilus influenzae* (Respiratory infections; meningitis; conjunctivitis; chancroid). Outer membrane proteins P1; P2 (b/c); P4(e); P5 (d); P6 (PAL; protein g); PCP; OMP26; D15; transferring binding proteins (Tbp); heme: hemopexin binding protein (HxuA). Vaccine proteins may be linked to lipooligosaccharides (LOS) to increase the antigenicity of the vaccine protein. see Foxwell et al., Microbiol Mol Biol Rev, 62:294-308 (1998); GTP-binding protein (lepA); outer membrane receptor-mediated transport energizer protein (TonB); protein-export membrane proteins (SecD: SecF); Hap and HWM1/HMW2 adhesive proteins; IgA1 protease. See: http://cmr.tigr.org/tigr-scripts/CMR/shared/AllGeneList.cgi?sub_org_val=ghi&feat_type=ORF; Webster et al., J. Histochem Cytochem 54:829-842 (2006); See Fleischmann and Adams, Science, 269:496-512 (1995); Berenson et al., Infection and Immunity, 73:2728-2735 (2005); Green et al., Infect Immun 59:3191-3198 (1991).

*Mycoplasma* (Atypical pneumonia; urogenital infections) membrane proteins p52, p67 (pMGA) and p77; Jan et al., Protein Expression and Purification; 7:160-166 (1996); Lipid-associated membrane proteins (LAMPs); See Lo et al., Clinical Infectious Diseases, 36:1246-53 (2003).

*Treponema* (syphilis): membrane protein (tmpA); Tp33 protein; membrane antigen, pathogen-specific (tpd); basic membrane protein (tpn39b); outer membrane proteins (tpn50; tmpB; ompH); membrane lipoproteins (tmpC); lipoproteins (tpp15; tpp17; tpn32); flagellar hook protein flgE; flagellar hook-basal body complex protein fliE; flagellar basal body rod proteins flgB; flgC; flgF; flgG; flagellar basal body rod modification protein flgD; flagellar P-ring protein flgI; flagellar protein flgJ; flagellar hook-associated proteins flgK and flgL; flagellar M-ring protein fliF; flagellar protein fliJ. See, McKevitt et al., Infection and Immunity, 73:4445-4450 (2005).

*Borrelia* (Relapsing fever; Lyme disease): Outer surface proteins (OspA; OspB; OspC). See, Anderton et al., Infection and Immunity, 72:2035-2044 (2004).

*Brucella* (Brucellosis) Outer Membrane protein 31 (Omp31); See Cassataro et al., Infection and Immunity; 73:8079-8088 (2005); Major OMPs Omp25 OMP31 and Omp2b; less abundant OMPs Omp10, Omp16, and Omp19; and smooth lipopolysaccharide (S-LPS). See Cloeckaert et al., Clinical and Diagnostic Laboratory Immunology; 6:627-629 (1999). Acidic-pH-inducible outer membrane protein (Aop). See *Brucella*: Molecular and Cellular Biology (López-Goñi and Ignacio Moriyón, eds.); Horizon Press (2004).

*Streptococcus* (Strep throat and other respiratory infections; skin and other abscesses; puerperal fever; opportunistic infections). M1 protein, a collagen-like surface protein; lepA. See Zhang et al., Proteomics; 7:1379-1390 (2007).

The preferred target vaccine proteins for bacteria may include peptides or proteins which are known to be produced by the bacteria, especially those which may be present on or near the surface of the bacterial outer membrane such that the target peptide or protein may be accessible to antibodies or cytotoxic T-cells which have been adapted to recognize the target peptide or target protein.

V. Host Cells

Lower eukaryotes such as yeast are preferred for expression of glycoproteins because they can be economically cultured, give high yields, and when appropriately modified are capable of suitable glycosylation. Yeast particularly offers established genetics allowing for rapid transformations, tested protein localization strategies and facile gene knock-out techniques. Suitable vectors have expression control sequences, such as promoters, including 3-phosphoglycerate kinase or other glycolytic enzymes, and an origin of replication, termination sequences and the like as desired.

Various yeasts, such as *K. lactis, Pichia pastoris, Pichia methanolica*, and *Hansenula polymorpha* are preferred for cell culture because they are able to grow to high cell densities and secrete large quantities of recombinant protein. Likewise, filamentous fungi, such as *Aspergillus niger, Fusarium* sp, *Neurospora crassa* and others can be used to produce glycoproteins of the invention at an industrial scale. Other suitable hosts include *Pichia finlandica, Pichia trehalophila, Pichia koclamae, Pichia mernbranaefaciens, Pichia minuta (Ogataea minuts, Pichia lindneri), Pichia opuntiae, Pichiiz thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula* sp., *Kluyveromyces* sp., *Candida albicans, Aspergillus nidulans, Aspergillus oryzae, Trichoderma reesei, Chrysosporium luchnowense, Fursarium gramineum, Fusarium venenatum* and *Physcomitrella patens*.

Lower eukaryotes, particularly yeast and filamentous fungi, can be genetically modified so that they express glycoproteins in which the glycosylation pattern is human-like or humanized. Such can be achieved by eliminating selected endogenous glycosylation enzymes and/or supplying exogenous enzymes as described by Gerngross et al., US 20040018590, the disclosure of which is hereby incorporated herein by reference. For example, a host cell can be selected or engineered to be impaired in initiating α-1,6 mannosyltransferase activity (outer chain initiation) with respect to the glycan on a glycoprotein, or is diminished or depleted in dolichy-P-Man:Man5GlcNAc2-PP-dolichyl α-1,3 mannosyltransferase activity, which would otherwise add mannose residues onto the N-glycan on a glycoprotein. Further, such a host cell, particularly a yeast or filamentous fungal host cell, should express or be engineered to express a mannosidase activity such as an α-1,2 mannosidase I activity, mannosidase II activity, mannosidase IIx activity and class III mannosidase activity. Host cells, particularly yeast and fungal hosts, are also engineered to express an N-acetylglucosamine transferase I (GnT) activity such as GnTI, GnTII, GnTIII, GnTIV, GnTV, GnTVI and GnTIX. Finally, enzymes to generate a pool of UDP-galactose, appropriate Golgi membrane transporters and a gene encoding a β-Galactosyl transferase (e.g., a β-GalT), yield a host strain that is capable of transferring a complex-type human N-glycan with terminal β-1,4-galactose. (Bobrowicz et al., Glycobiology; 14:757-66 (2004)).

VI. Introduction of α-GalT Into a Glycoengineered Hybrid N-glycan producing Yeast Strain A glycoengineered *P. pastoris* strain that secretes proteins with mammalian hybrid N-glycans containing terminal Glc-NAc such as PBP3 is generated by elimination of a portion of a yeast type N-glycosylation (such as PpOCH1) and expressing an α-1,2-MNS1 and GnTI enzymes properly localized in the endoplasmic reticulum (Choi et al, PNAS, 2003; Bobrowicz et al., Glycobiology; 14:757-66 (2004)). Further, a strain that secretes hybrid mammalian N-glycans with terminal β-1,4-galactose, such as RDP39-6, is generated by further expression of hβ-GalTI as well as UDP-Galactose 4-epimerase (Davidson et al., US Patent Application 2006/0040353, the disclosure of which is hereby incorporated herein). Expression of UDP-Gal transporter can further enhance β-1,4-galactose transfer (Davidson et al., US Patent Application 2006/0040353). To obtain a terminal α-1,3-galactosyl epitope expressing strain, a further plasmid expressing an α-1,3-galactosyl transferase that is properly targeted to the endoplasmic reticulum is transformed into this β-1,4-galactose terminated hybrid N-glycan producing strain. Transformants are selected on standard yeast selective medium such as that containing Nourseothricin or Hygromycin for which the plasmid contains a resistance gene and correct integrants were screened by yeast cell lysate PCR. Recombinants are then screened for functional expression of properly targeted α-1,3-galactosyl transferase by analyzing N-glycans released by PNGase F digest of the secreted reporter protein such as K3 by Matrix-Assisted Laser Desorption/Ionization Time of Flight Mass Spectrometry (MALDI-TOF MS). Correct addition of α-1,3-galactose to the hybrid α-1,4-galactose terminated acceptor N-glycan is identified by masses that are observed consistent with addition of a single α-linked galactose residue to the GFI3.5

N-glycan (β-Gal)GlcNAcMan5GlcNAc2 of RDP39-6 to yield the GFI5.7 (α-Gal)(β-Gal)GlcNAcMan5GlcNAc2 N-glycan.

VII. Vaccine Compositions

The lower eukaryotic host cells of the present invention can be used to express vaccine proteins, and in preferred embodiments, vaccine glycoproteins. The vaccine protein or glycoprotein can be formulated with other pharmaceutically acceptable active agents and/or inactive excipients to form vaccine glycoprotein compositions. The vaccine glycoproteins compositions of the present invention comprise an N-glycan comprising a terminal α-galactosyl residue. In certain embodiments, N-glycan comprising a terminal α-galactosyl residue is the predominant N-glycan, In preferred embodiments, the predominant N-glycan comprises at least 30 mole percent, preferably at least 40 mole percent and more preferably at least 50 mole percent of the N-glycans present on the glycoprotein in the composition. In particular preferred embodiments, the predominant N-glycan is selected from the group consisting of (α-Gal)(β-Gal)GlcNAcMan5GlcNAc2; (α-Gal)(β-Gal)2GlcNAc2Man3GlcNAc2; and (α-Gal)2(β-Gal)2GlcNAc2Man3GlcNAc2.

The vaccine compositions of the present invention preferably comprise vaccine glycoprotein which is of viral or bacterial origin. The vaccine glycoprotein is preferably a glycoprotein which is naturally glycosylated. Alternatively, the vaccine glycoprotein may comprise a glycoprotein that has been synthetically produced, and in particular may comprise a glycoprotein which has been genetically engineered to create one or more N-glycosylation sites not otherwise present in the native protein. In certain embodiments, the vaccine compositions may comprise an epitopic peptide derived from cancer cells. In these embodiments, the vaccine composition may comprise an epitopic glycopeptide sequence derived from an epitopic peptide from a cancer cell or tumor cell antigen. In preferred embodiments, the epitopic peptide is selected from the group consisting of a Her-2 epitope, a neu epitope or a prostate stem cell antigen (PSCA) epitope. In certain preferred embodiments, the vaccine composition may comprise a compound vaccine composition, comprising multiple vaccine proteins or vaccine glycoproteins. In such cases, the vaccine proteins or vaccine glycoproteins may comprise multiple vaccine glycoproteins directed to the same target virus, bacterium or other epitopic peptide; or may comprise vaccine glycoproteins directed to multiple distinct viruses, bacteria and/or epitopic peptides, such as epitopic peptides directed to a cancer cell or tumor cell.

In the following examples, viral vaccine glycoproteins are expressed in host cells of the species *Pichia pastoris*. These examples demonstrate the invention with respect to specific preferred embodiments of the invention, and are not limiting in any manner. The skilled artisan, having read the disclosure and examples herein, will recognize that numerous variants, modifications and improvements to the methods and materials described are possible without deviating from the practice of the present invention.

EXAMPLES

I. Cloning of Alpha 1,3-Galactose Transferase

The gene encoding a *Mus Musculus* α-1,3-galactosyl transferase but lacking the putative transmembrane Golgi localization domain (MmαGalT) was amplified by polymerase chain reaction using mouse Kidney cDNA (Clontech) as a template and primers RCD446 (TTGGCGCGC-CAACAGCCCAGACGGCTCTTTCTTG) (SEQ ID NO: 1) and RCD447 (GGTTAATTAATCAGACATT-ATTTCTAACCAAATT) (SEQ ID NO: 2). The resulting product was cloned into the pCR2.1 Topo vector (Invitrogen), sequenced, and named pRCD680. The MmαGalT gene was digested from pRCD680 using AscI/PacI and cloned into plasmid pRCD508, a pUC19-based plasmid containing the human β-1,4-galactosyl transferase I catalytic domain flanked by AscI/PacI sites (the human domain was excised in the present construct), the 5' 108 nucleotides of the *Saccharomyces cerevisiae* MNN2 gene, encoding in-frame the N-terminal transmembrane Golgi localization domain, the *Pichia pastoris* GAPDH promoter and *S. cerevisiae* CYCI transcriptional terminator, flanking regions to knock out the *P. pastoris* ARM gene as an integration site, and the *P. pastoris* HIS1 gene as a selectable marker. This plasmid was named pRCD683 and yields a Pparg1:HIS1 expression construct containing a fusion gene encoding the yeast localization domain of *S. cerevisiae* Mnn2p and the catalytic domain of the MmαGalT protein. Plasmid pRCD683 was digested with SfiI to linearize and liberate the pUC19 bacterial sequences for transformation into *P. pastoris*.

II. Generation of a Suitable Recipient Host Strain for α-GalT

Non-human N-glycans containing terminal α-1,3-galactose are complex-type N-glycans generated by addition of an α-1,3-linked galactose residue to a mammalian N-glycan intermediate structure containing terminal β-1,4-galactose. These glycans result from competition for the terminal β-1,4-galactose by SialT and α-GalT. To eliminate such competition, a glycoengineered yeast strain was chosen as the starting strain. The strain contained the enzymes needed to produce complex type human N-glycans with terminal β-1,4-galactose, but specifically lacking SialT.

A glycoengineered *P. pastoris* yeast strain was generated in which the typical yeast-type N-glycosylation was modified to instead produce fully sialylated human N-glycans. First, deletion of the yeast gene OCH1 eliminated the enzyme activity responsible for 'outer chain' glycosylation (Choi et al, *Proc Natl Acad Sci US*; 100:5022-7 (2003)). Subsequently, a mannosidase I (MNSI) gene and GlcNAc transferase I (GnTI) gene were engineered into this strain and properly localized to the secretory pathway to efficiently generate mammalian hybrid-type N-glycans (Choi et al, 2003). In a further step, a mannosidase II (MNSII) gene and GlcNAc transferase II (GnTII) gene were engineered into the strain and properly localized to the secretory pathway to efficiently generate mammalian complex-type N-glycans (Hamilton et al, Science; 301:1244-6. (2003)). Finally, by further engineering into this strain enzymes to generate a pool of UDP-galactose, appropriate Golgi membrane transporters and a gene encoding β-Galactosyl transferase (β-GalT), a yeast strain was generated that is capable of transferring a complex-type human N-glycan with terminal β-1,4-galactose. (Bobrowicz et al., *Glycobiology*; 14:757-66 (2004)). A yeast strain producing predominantly terminal β-1,4-galactose is a suitable host strain to receive a properly localized catalytically active α-GalT.

III. Introduction of α-GalT Into a Glycoengineered Yeast Strain

RDP109 is a his1 mutant glycoengineered *P. pastoris* strain that secretes proteins with mammalian complex N-glycans containing terminal β-1,4-galactose. RDP109 was generated by elimination of the yeast mannosyltransferase Och1p and phosphomannosyltransferases Mnn4 bp and Pno1p and introduction of secretory pathway localized gene fusions encoding the mammalian enzymes MNS1, GnTI, MNSII, GnTII, β-GalTI, as well as genes encoding Golgi UDP-GlcNAc and UDP-Gal transporters and UDP-Galactose 4-epimerase (See Gerngross, U.S. Pat. No. 7,029,872; Davidson et al., US Patent Application 2006/0040353; and Bobrowicz, US Patent Application 2006/0211085, the disclosure of which are each hereby incorporated herein). RDP109 also expresses the Kringle 3 domain of human Plasminogen (K3) as a secreted reporter protein (Choi et al, *Proc Natl Acad Sci US;* 100:5022-7 (2003)). Transformants were selected on medium lacking histidine and correct integrants were screened by replica-plating transformants to medium lacking arginine. HIS+/arg-recombinants were then screened for functional expression of properly targeted α-1,3-galactosyl transferase by analyzing N-glycans released by PNGaseF digest of the secreted reporter protein K3 by Matrix-Assisted Laser Desorption/Ionization Time of Flight Mass Spectrometry (MALDI-TOF MS). Two transformants, designated RDP241 and RDP242, were identified in which masses were observed consistent with addition of one and two α-linked galactose residues to the GFI5.0 N-glycan (β-Gal)2GlcNAc2Man3GlcNAc2 of RDP109 to yield the GFI5.8 (α-Gal)(β-Gal)2GlcNAc2Man3GlcNAc2 and GFI5.9 (α-Gal)2(β-Gal)2GlcNAc2Man3GlcNAc2 N-glycans respectively (see FIGS. 4A-4B).

IV. Optimization of Leader Localization Sequence for β-1,4-GalT Via a Combinatorial Library The N-glycans produced by strains RDP109, RDP241 and RDP242 include significant amounts of hybrid-type N-glycans (see FIGS. 1, 4A-4B). Therefore, a library of strains was created to screen for an optimal leader localization sequence for human β-1,4-galactosyltransferase I (hβ-GalTI) (similar to strategy employed in Choi et al, 2003). Strain PBP235 is a yeast strain that was glycoengineered to produce complex triantennary mammalian N-glycans with terminal GlcNAc. This strain was generated by introducing localized mMNS1 (m=mouse), hGnTI (h=human), dMNSII (d=*drosophila*), hGnTII and hGnTIVb gene fusions into a strain in which the yeast N-glycosylation machinery (PpOCH1 (Pp=*Pichia pastoris*), PpPNO1, PpMNN4B, and PpPBS2) was eliminated. This strain was transformed with a series of constructs containing fusion genes of different leader/localization domains fused in frame to the hβGalTI. Previously (Davidson et al., US 20060040353), a fusion gene encoding the N-terminal 36aa of *S. cerevisiae* Mnn2p was utilized for localization of hβGalTI as well as for hGnTII, dMNSII, and also here for hGnTIV. This resulted in a significant percentage of hybrid-type glycans and also biantennary N-glycans. We hypothesized that this might be due to competition between hβGalTI and either or all of dMNSII, hGnTII, and hGnTIV. The screening of a library of hβGalTI constructs revealed several in which the hybrid N-glycans and biantennary N-glycans were reduced. One of these constructs that yielded reduced hybrid and biantennary N-glycans contained a fusion gene encoding the N-terminal 58aa of *S. cerevisiae* Mnt1p (ScMntI1-58) (Sc=*S. cerevisiae*) fused to hβGalTI.

Figure 3:
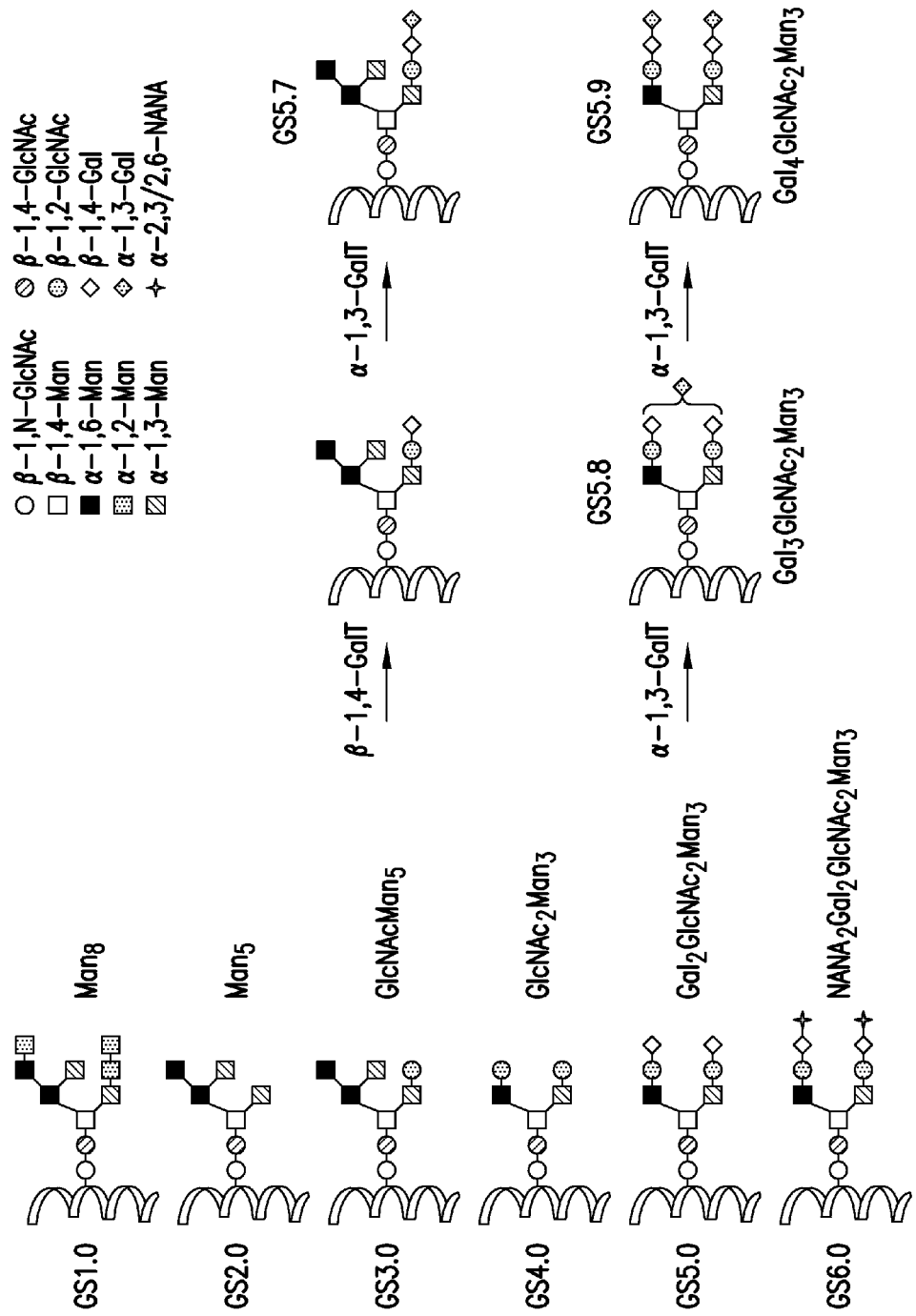
FIG. 3. Stepwise modification of the yeast N-glycosylation machinery. Humanization of yeast N-linked glycans results in a series of yeast strains capable of producing human/mammalian intermediate N-glycan structures. A yeast strain capable of producing such a GS5.0 intermediate N-glycan, (β-Gal)2GlcNAc2Man3GlcNAc2, can be modified to produce a uniform GS5.9 N-glycan, (α-Gal)2(β-Gal)2GlcNAc2Man3GlcNAc2, by engineering of an active, properly localized α-GalT in the absence of a sialyl transferase.
Figure 4A:
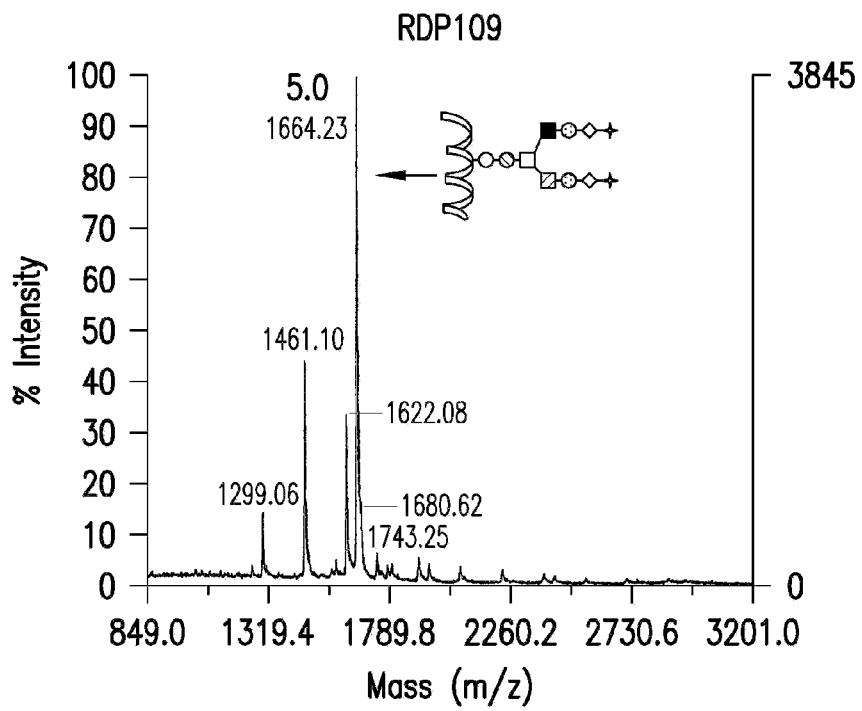
FIGS. 4A & 4B. A GFI5.0 glycoengineered yeast strain expressing α-GalT yields N-glycans with terminal α-gal. Here, a non-optimized mouse α-1,3-GalT was engineered into a non-optimized GFI5.0 humanized *P. pastoris* yeast strain. This strain expresses the Kringle 3 domain of human plasminogen under control of the strong, inducible AOX1 promoter. Secreted K3 protein was produced by induction in methanol-containing medium, purified by Ni++ affinity chromatography and N-glycans were released by PNGase F digestion and subjected to MALDI-TOF MS. The α-GalT activity can be observed by the appearance of α-Gal containing peaks (GS5.8 and GS5.9) in a MALDI-TOF MS. 2.0, Man5GlcNAc2; 5.0, (β-Gal)2GlcNAc2Man3GlcNAc2; 5.8, (α-Gal)(β-Gal)2GlcNAc2Man3GlcNAc2; 5.9, (α-Gal)2(β-Gal)2GlcNAc2Man3GlcNAc2.
Figure 4B:
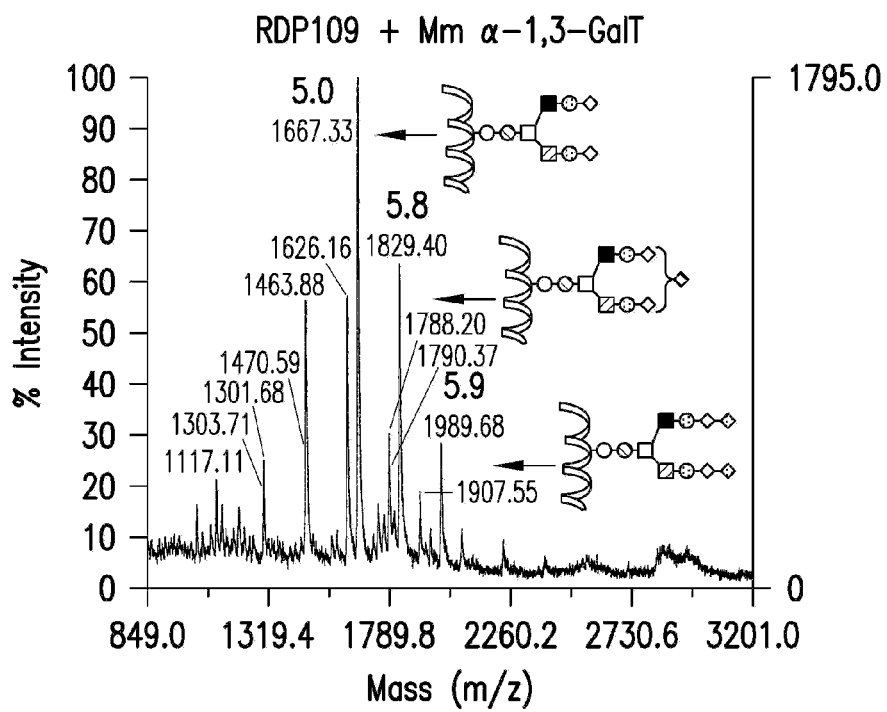
Figure 5A:
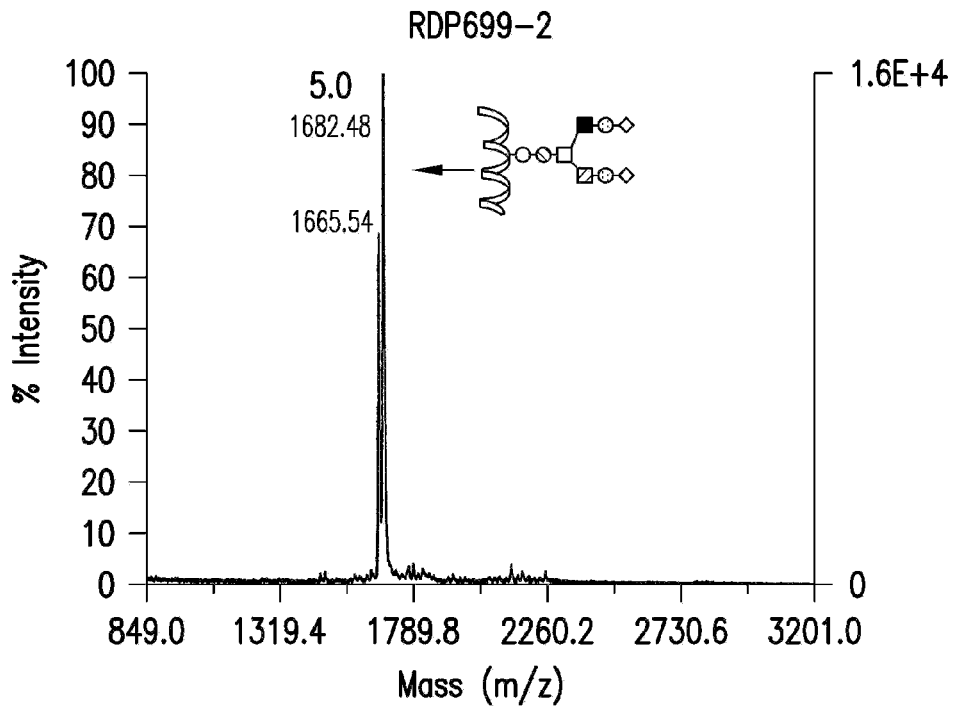
FIGS. 5A & 5B. Optimization of the upstream glycosylation machinery in a GFI5.0 glycoengineered yeast strain expressing α-GalT increases the uniformity of the N-glycans. Here a mouse α-1,3-GalT, not codon optimized or localization optimized, was engineered into an optimized GFI5.0 humanized *P. pastoris* yeast strain. This strain expresses rat recombinant EPO under control of the strong AOX1 promoter. Secreted His-tagged rrEPO protein was produced by induction in methanol containing medium, purified by Ni++ affinity chromatography and N-glycans were released by PNGase F digestion and subjected to MALDI-TOF MS. Active α-GalT can be observed by the appearance of α-Gal containing peaks (GS5.8 and GS5.9) in a MALDI-TOF MS. 2.0, Man5GlcNAc2; 5.0, (β-Gal)2GlcNAc2Man3GlcNAc2; 5.8, (α-Gal)(β-Gal)2GlcNAc2Man3GlcNAc2; 5.9, (α-Gal)2(β-Gal)2GlcNAc2Man3GlcNAc2.
Figure 5B:
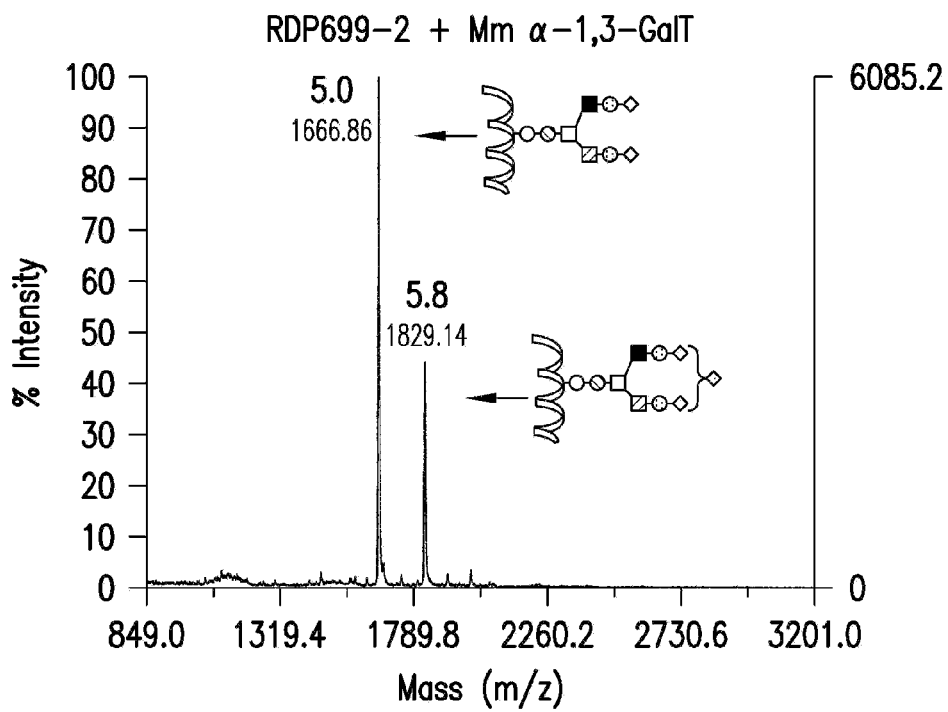

Using the data from the combinatorial library screen for hβGalTI leader sequences a strain, RDP699-2, was created which secretes proteins with complex mammalian N-glycans with nearly homogeneous terminal β-1,4-linked galactose (GS5.0, FIGS. 3, 5A). This strain has been glycoengineered to eliminate yeast-type N-glycosylation and expresses localized fusions of mMNSI, hGnTI, dMNSII, hGnTII, and hβGalTI. Based on the combinatorial library screen, the hβGalTI is a fusion gene encoding ScMntI1-58 as a localization domain. Because of the improved leader localization, this strain has significantly reduced hybrid-type N-glycans compared to a previous generation strain such as RDP109, RDP241 and RDP242. Strain RDP699-2 also produces rat Erythropoeitin (rEpo) as a secreted reporter protein and is arg-because the PpARG1 gene was been deleted. Plasmid pGLY1443 contains a fusion gene encoding ScMntI1-58 fused to the catalytic domain of mαGalT (from pRCD680) described above and contains PpARG1 as a selectable marker. Plasmid pGLY1443 was transformed into strain RDP699-2 and transformants were selected on medium lacking arginine, resulting in strain RDP1030. Analysis of N-glycans released by PNGaseF digest from RDP1030 by MALDI-TOF revealed the presence of both GFI5.8 (α-Gal)(β-Gal)2GlcNAc2Man3GlcNAc2 and GFI5.9 (α-Gal)2(β-Gal)2GlcNAc2Man3GlcNAc2 N-glycans (FIG. 5B) via addition of one and two α-1,3-galactose residues to the GFI5.0 (β-Gal)2GlcNAc2Man3GlcNAc2 structure. However, the hybrid N-glycans present in FIGS. 4A-4B are nearly undetectable (compare FIGS. 4A-4B with FIGS. 5A-5B), resulting from the improved localization of hβGalTI and presumably from reduced competition of hβGalTI with dMNSII and hGnTII for hybrid substrates.

V. Screening a Library of α-1,3-GalTs Improves α-Gal Transfer

Figure 6A:
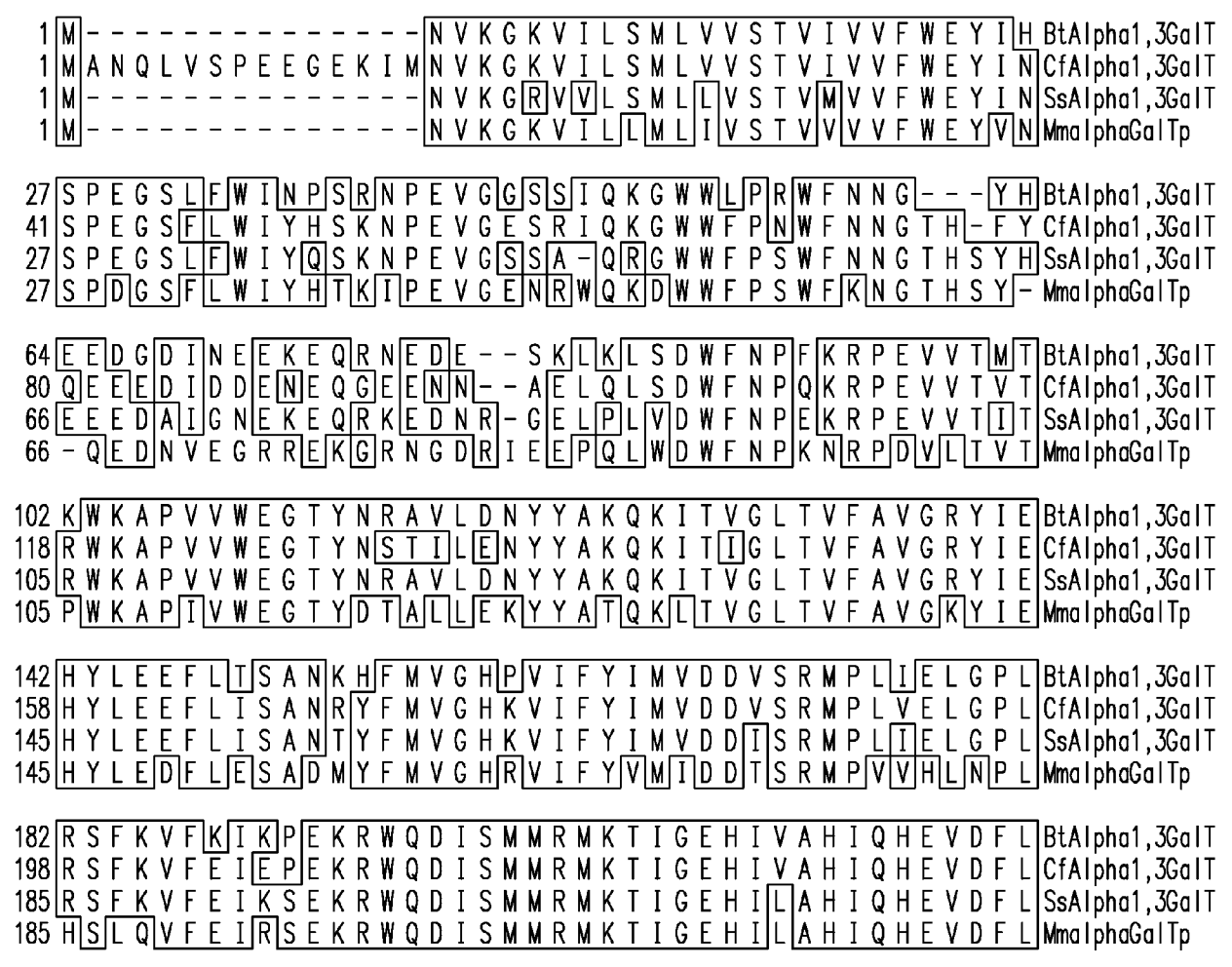
Figure 7A:
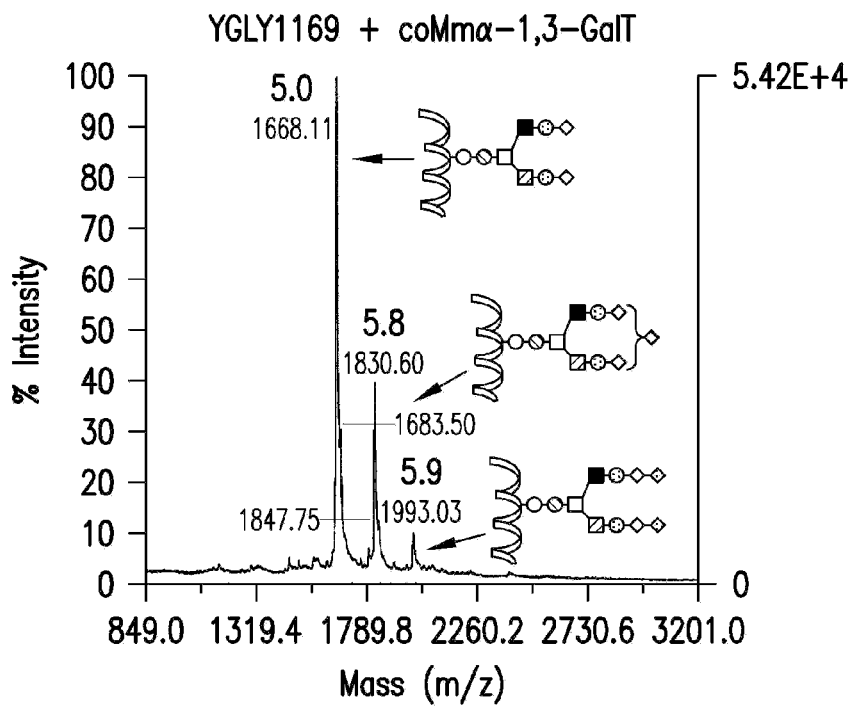
FIGS. 7A-7C. Expression of a library of α-GalTs and codon optimization for *P. pastoris* improves α-Gal transfer. Here codon optimized, but not localization optimized, *M. musculus* α-1,3-GalT, *S. scrofa* α-1,3-GalT, *C. familiaris* α-1,3-GalT were engineered into an optimized GFI5.0 humanized *P. pastoris* yeast strain. This strain expresses rrEPO under control of the strong, inducible AOX1 promoter. Secreted His-tagged rrEPO protein was produced by induction in methanol containing medium, purified by Ni++ affinity chromatography and N-glycans were released by PNGase F digestion and subjected to MALDI-TOF MS. The α-GalT activity can be observed by the appearance of α-Gal containing peaks (GS5.8 and GS5.9) in a MALDI-TOF MS. 2.0, Man5GlcNAc2; 5.0, (β-Gal)2GlcNAc2Man3GlcNAc2; 5.8, (α-Gal)(β-Gal)2GlcNAc2Man3GlcNAc2; 5.9, (α-Gal)2(β-Gal)2GlcNAc2Man3GlcNAc2.
Figure 7B:
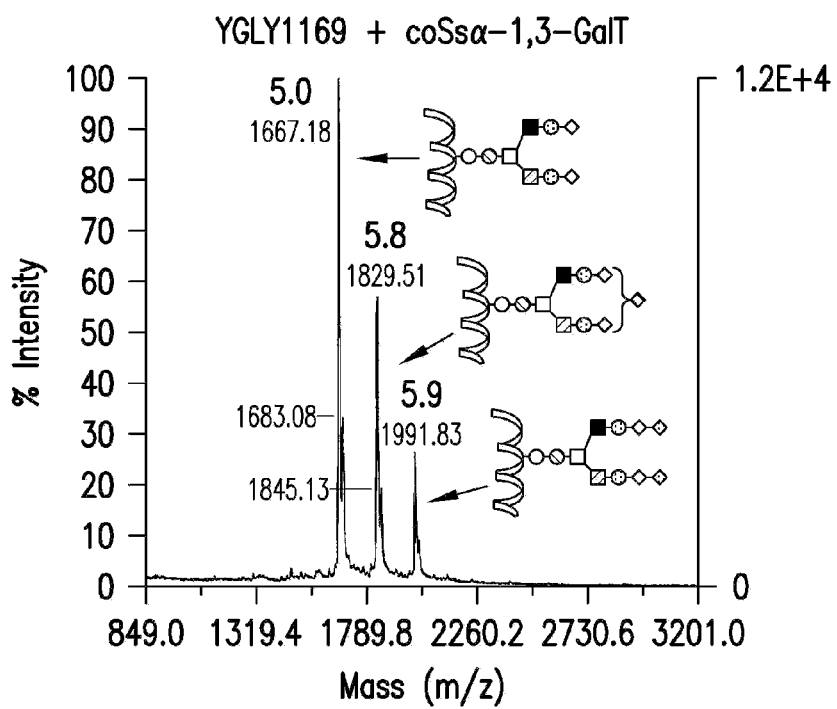
Figure 7C:
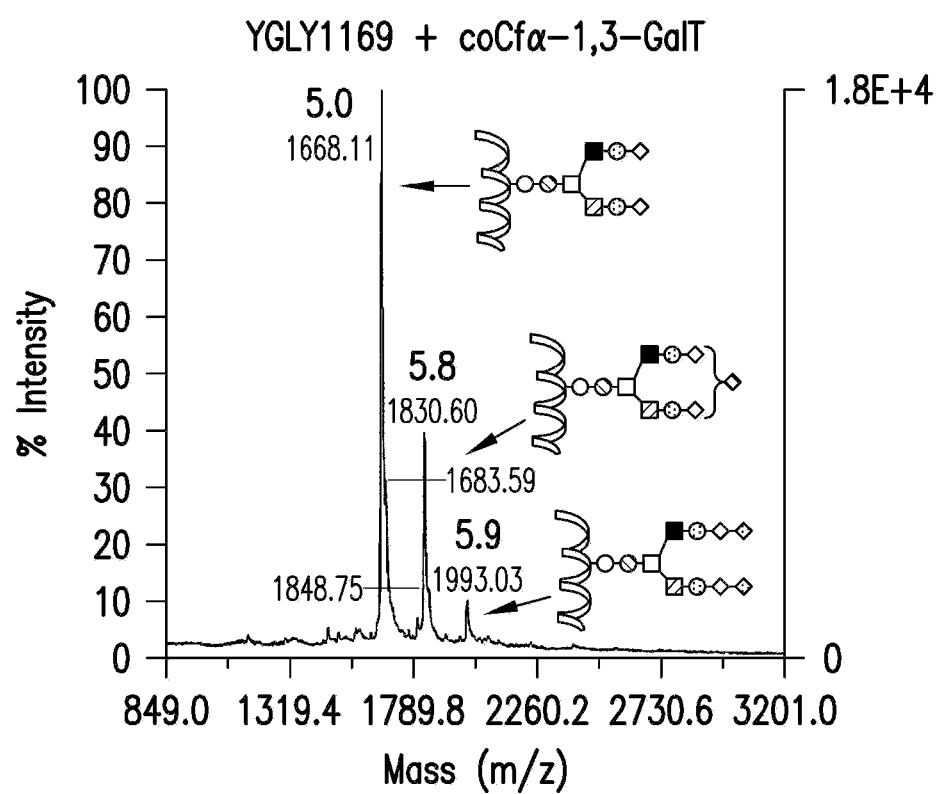

*P. pastoris* strain YGLY1169, a strain similar to RDP699-2, was created and secretes proteins with complex mammalian N-glycans with terminal β-1,4-linked galactose ((β-Gal)2GlcNAc2Man3GlcNAc2 GS5.0, FIG. 3). This strain has been glycoengineered to eliminate yeast-type N-glycosylation and expresses localized fusions of mMNSI, hGnTI, dMNSII, hGnTII, and hβGalTI. Based on the combinatorial library screen, the hβGalTI is a fusion gene encoding ScMntI1-58 as a localization domain. Because of the improved leader localization, this strain has significantly reduced hybrid-type N-glycans compared to a previous generation strain such as RDP109 and is thus similar to RDP699-2 (not shown). This strain is also ura- because the PpURA5 gene has been deleted. Plasmids were created containing gene fusions encoding ScMntI1-58 fused to the catalytic domain of various α-GalTs (FIG. 6A-6B) including those from *Mus musculus* (pGLY1892), *Sus scrofa* (pGLY1893) and *Canis familiaris* (pGLY1894). These plasmids all contain the PpURA5 gene as a selectable marker. Plasmids pGLY1892, 1893, and 1894 were transformed into strain YGLY1169 and transformants were selected on medium lacking uracil, resulting in strains YGLY1783, YGLY1785, and YGLY1787, respectively. These strains were each transformed with plasmid pSH692, containing a gene encoding rEPO as a secreted reporter, and the shBLE gene as a selectable marker. Plasmid pSH692 was transformed into strains YGLY1783, YGLY1785, and YGLY1787 and N-glycans released by PNGaseF digest from the resulting transformants were analyzed from secreted rEPO by MALDI-TOF. The N-glycans were similar to that obtained from strain RDP1030 (FIGS. 7A-7C). However, an incremental improvement in the α-gal transfer was observed from introduction of *Sus scrofa* αGalT (SsαGalT) compared to MmαGalT, as judged by the relative intensity of peaks corresponding to GFI5.0 (β-Gal)2GlcNAc2Man3GlcNAc2, GFI5.8 (α-Gal)(β-Gal)2GlcNAc2Man3GlcNAc2 and GFI5.9 (α-Gal)2(β-Gal)2GlcNAc2Man3GlcNAc2, (FIG. 7B).

VI. Optimization of Leader Localization Sequence for SsαGalT via a Combinatorial Fusion Library Improves α-Gal Transfer In order to improve α-galactose transfer, a library of plasmids was created to screen for optimal leader localization sequences for SsαGalT, based on plasmid pGLY2169.

Figures 8A, 8B:
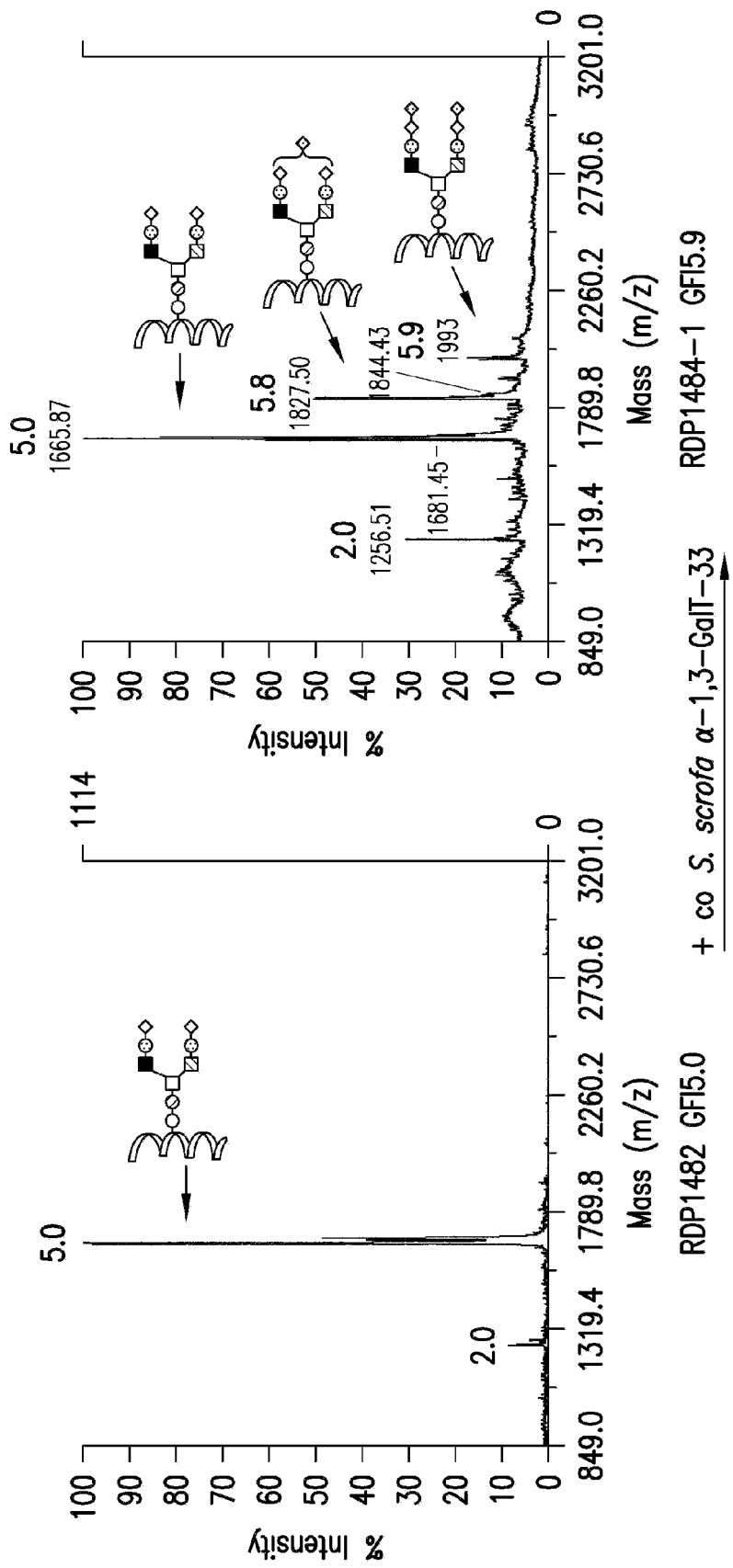
FIGS. 8A & 8B. Expression of Kringle 3 in a strain with *S. scrofa* α-1,3-GalT localized with ScMnt11-58 yields similar N-glycans to that observed with rrEPO. Here an ovine α-1,3-GalT, codon optimized, but not localization optimized, was engineered into an optimized GFI5.0 humanized *P. pastoris* yeast strain. This strain expresses the Kringle 3 domain of human plasminogen under control of the strong, inducible AOX1 promoter. Secreted His-tagged K3 protein was produced by induction in methanol containing medium, purified by Ni++ affinity chromatography and N-glycans were released by PNGase F digestion and subjected to MALDI-TOF MS. The α-GalT activity can be observed by the appearance of α-Gal containing peaks (GS5.8 and GS5.9) in a MALDI-TOF MS. 2.0, Man5GlcNAc2; 5.0, (β-Gal)2GlcNAc2Man3GlcNAc2; 5.8, (α-Gal)(β-Gal)2GlcNAc2Man3GlcNAc2; 5.9, (α-Gal)2(β-Gal)2GlcNAc2Man3GlcNAc2.
Figure 9:
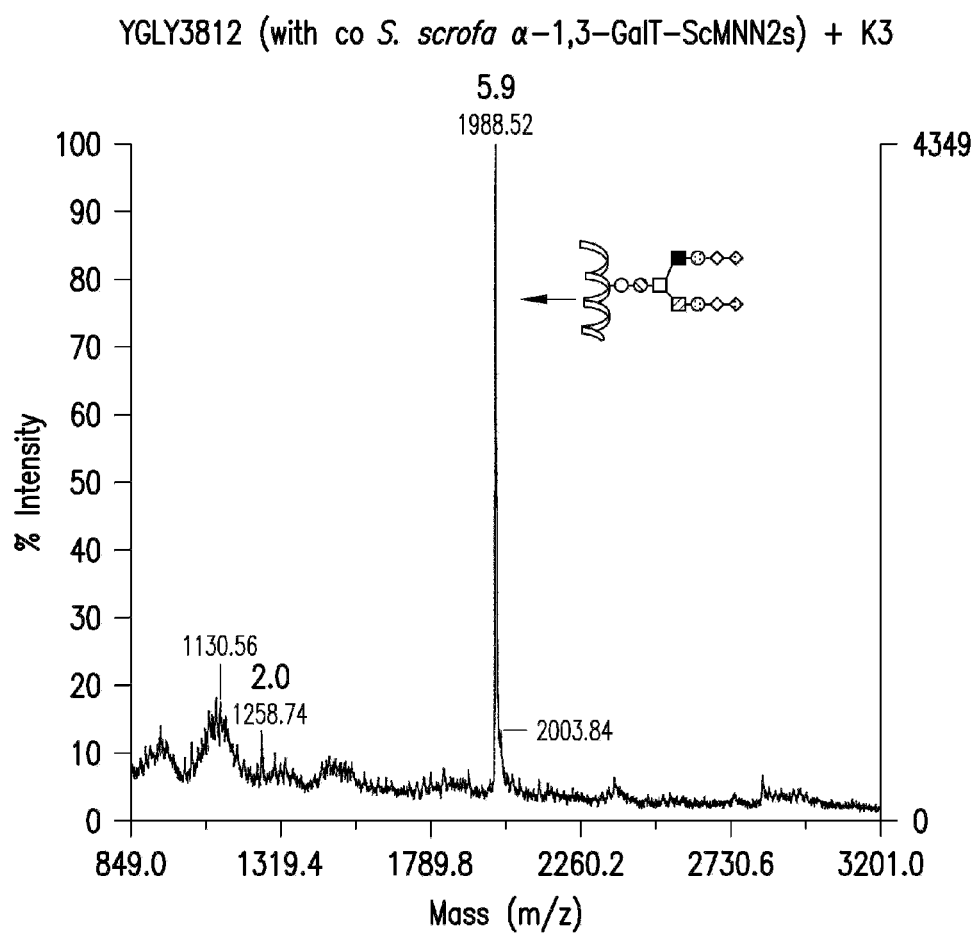
FIG. 9. Optimization of the leader localization of the α-GalT introduced into a GFI5.0 strain increases the amount of terminal α-gal transferred to N-glycans. Here an ovine α-1,3-GalT, codon optimized, and localization optimized with ScMnn21-36, was engineered into an optimized GFI5.0 humanized *P. pastoris* yeast strain. This strain expresses the Kringle 3 domain of human plasminogen under control of the strong AOX1 promoter. Secreted His-tagged K3 protein was produced by induction in methanol containing medium, purified by Ni++ affinity chromatography and N-glycans were released by PNGase F digestion and subjected to MALDI-TOF MS. The α-GalT activity can be observed by the appearance of α-Gal containing peaks (GS5.9) in a MALDI-TOF MS. In this mature GFI5.9 strain, GS5.9 can be observed as the predominant N-glycan. 2.0, Man5GlcNAc2; 5.9, (α-Gal)2(β-Gal)2GlcNAc2Man3GlcNAc2.

Plasmid pGLY2169 contains the gene encoding the catalytic domain of SsαGalT without a yeast localization domain, but instead a pair of restriction sites, NotI and AscI and also contains the NAT gene gene (encoding for resistance to the aminoglycoside Nourseothricin) as a selectable marker. A library of DNA sequences encoding yeast localization domains (numbered 33-67, 745-756) was cloned into this vector using NotI/AscI and the resulting plasmids named pGLY2169-33-pGLY2169-756. This library of plasmids was transformed into P. pastoris strain RDP1482 and transformants were selected on medium lacking uracil. Strain RDP1482 has been engineered to secrete proteins with complex mammalian N-glycans with terminal β-1,4-linked galactose (GS5.0 (β-Gal)2GlcNAc2Man3GlcNAc2, FIG. 3), and expresses localized fusions of mMNSI, hGnTI, dMNSII, hGnTII, and hβGalTI. Again, based on the combinatorial library screen, the hβGalTI is a fusion gene encoding ScMntI1-58 as a localization domain. Strain RDP1482 has also been engineered to secrete the K3 domain of human plasminogen as a reporter protein under control of the AOX1 promoter. K3 was produced by inducing cultures on methanol as a sole carbon source, and supernatant protein was purified from transformants and N-glycans released by PNGase digest were analyzed by MALDI-TOF. The results indicated that when the ScMntI1-58-SsαGalT fusion gene was expressed, a similar ratio of GFI5.0, GFI5.8, and GFI5.9 N-glycans were observed compared transformants of strain YGLY1785 (FIGS. 8A-8B). However, several leader/localization domain-SsαGalT fusions including revealed a significant increase in α-gal transfer as judged by the ratio of GFI5.0, GFI5.8 and GFI5.9 masses observed. For a single leader-SsαGalT fusion, ScMnn21-36-SsαGalT, GFI5.9 was the only peak that was observed, indicating almost quantitative transfer of α-gal to the β-1,4-galactose substrate (FIG. 9).

VII. Expression of Influenza A HA Protein in a GFI5.9 Strain

Figure 10:
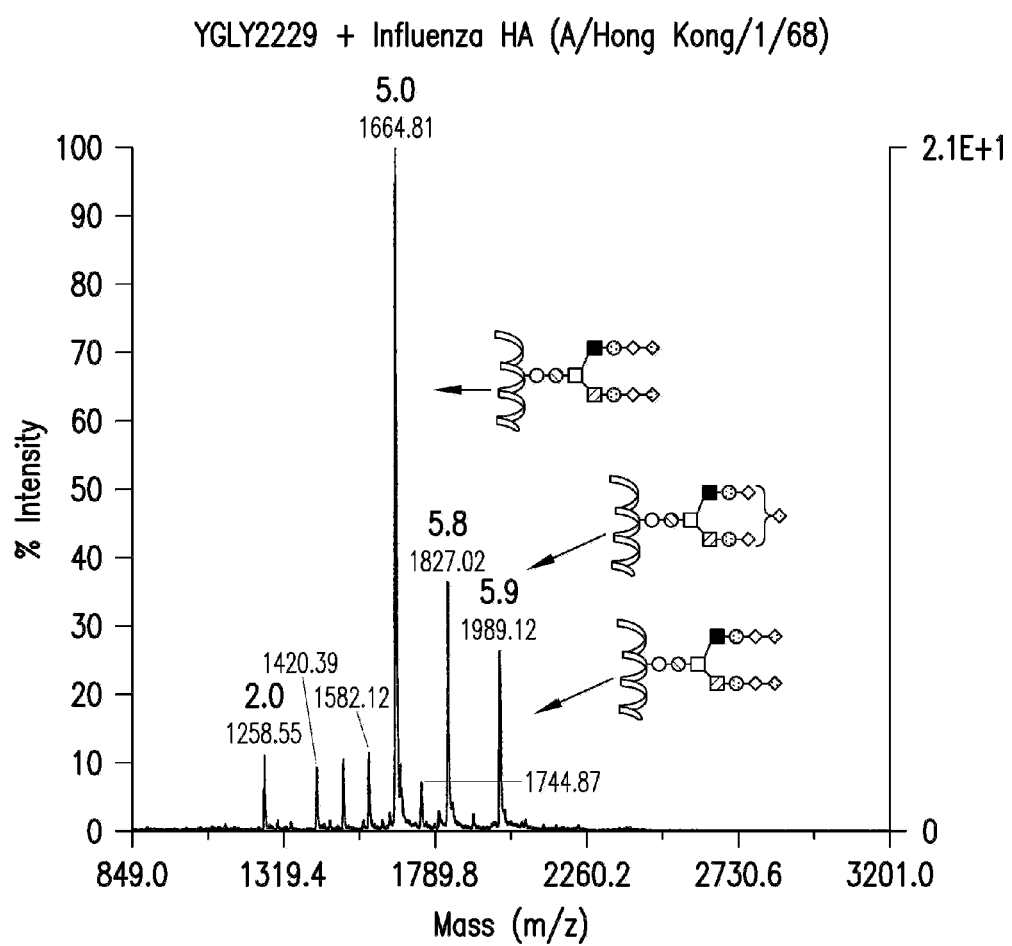
FIG. 10. Expression of an Influenza HA ectodomain protein in a GFI5.9 glycoengineered *P. pastoris* yeast strain. This strain contains ovine α-1,3-GalT, codon optimized, but not localization optimized, engineered into an optimized GFI5.0 humanized *P. pastoris* yeast strain. Expression of His-tagged Influeza HA (A/Hong Kong/1/58 variant) ectodomain was demonstrated by Western blot analysis of culture supernatant, then Ni++ affinity chromatography purified protein was subjected to PNGase F digestion and MALDI-TOF MS analysis. 2.0, Man5GlcNAc2; 5.0, (β-Gal)2GlcNAc2Man3GlcNAc2; 5.8, (α-Gal)(β-Gal)2GlcNAc2Man3GlcNAc2; 5.9, (α-Gal)2(β-Gal)2GlcNAc2Man3GlcNAc2.

DNA sequences encoding the ectodomain (i.e. lacking the C-terminal transmembrane domain) of several representative Influenza A type H3 HA proteins including HA Hong Kong (pGLY2766) [SEQ ID NO: 3], HA Panama (pGLY2764), HA Sydney (pGLY2765), HA New York (pGLY2762), and HA Moscow (pGLY2763), and several representative type H1 HA proteins including HA Beijing (pGLY2760), HA New Calcedonia (pGLY2759), HA Puerto Rico (pGLY2761), and HA South Carolina (pGLY2767) [SEQ ID NO: 4] were synthesized and cloned (GeneArt, LLC). Each of these plasmids was subcloned into a P. pastoris expression vector containing the AOX1 promoter and ShBLE drug resistance marker and fused in frame with a library of secretion signal peptides, including the S. cerevisiae α-Mating Factor prepro secretion signal. GFI5.9 glycoengineered P. pastoris strain YGLY2229 was transformed with each of the Influenza HA-containing expression plasmids and colonies were selected on minimal medium containing 300 mg/L Zeocin. Several transformants were selected and cultivated in 96 well deep well plates for 72 h at 26 C in liquid medium with glycerol as the sole carbon source, then centrifuged and resuspended in medium with methanol as the sole carbon source and incubated at 26 C for 24 hours. Cells were centrifuged and 7 ul of supernatant was subjected to standard Western blot analysis under non-reducing conditions and probing with a pre-labeled anti-HIS (H3 HIS probe, Santa Cruz) antibody. A band of appropriate size was observed for each HA expressed. Approximately 600 ul of supernatant was subjected to Ni-affinity purification, PNGase digestion to remove N-glycans, and MALDI-TOF MS analysis. N-glycan masses corresponding to GS5.0, GS5.8 and GS5.9 glycoforms were observed for all Influenza HA proteins tested. As an example, N-glycans from Influenza A HA Hong Kong fused in frame with the S. cerevisiae alpha mating factor prepro secretion signal (pGLY2922) expressed in YGLY2229 are shown (FIG. 10).

Figure 11:
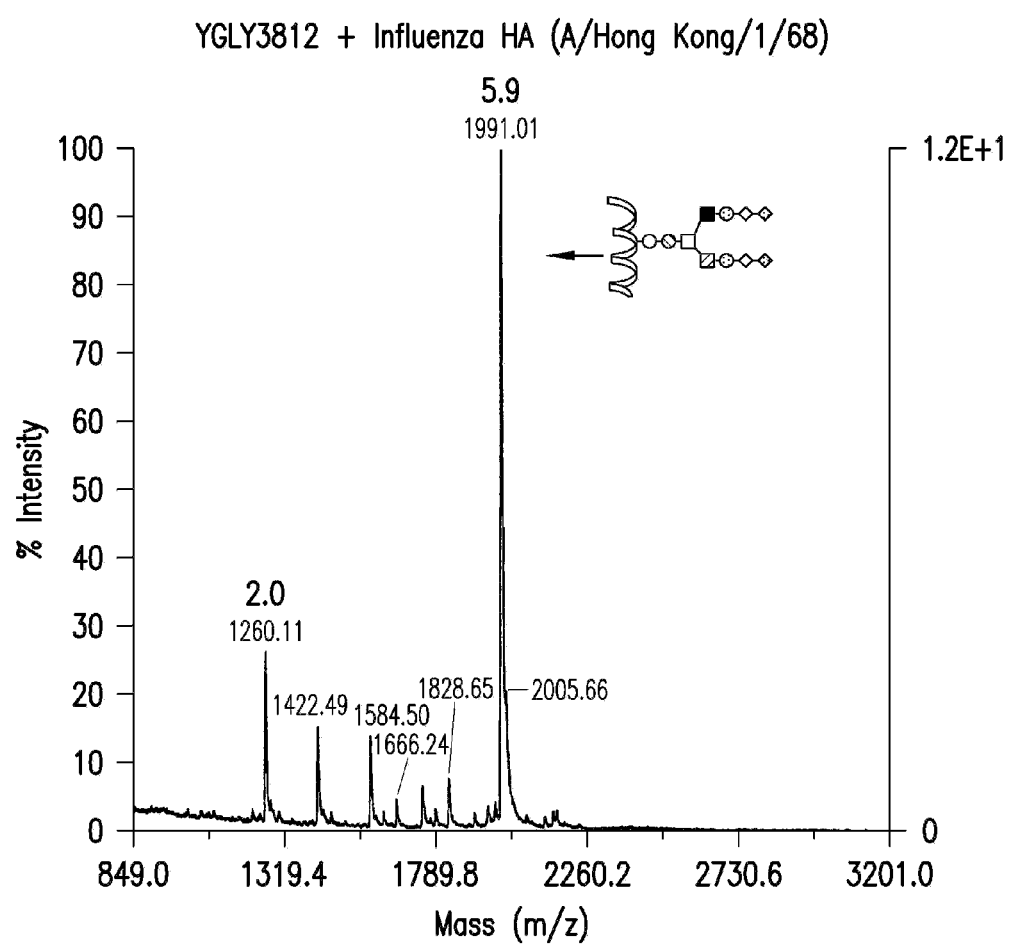
FIG. 11. Expression of an Influenza HA ectodomain protein in a GFI5.9 glycoengineered *P. pastoris* yeast strain. This strain contains ovine α-1,3-GalT, codon optimized and localization optimized, engineered into an optimized GFI5.0 humanized *P. pastoris* yeast strain. Expression of His-tagged Influeza HA (A/South Carolina/1/18 variant) ectodomain was demonstrated by Western blot analysis of culture supernatant, then Ni++ affinity chromatography purified protein was subjected to PNGase F digestion and MALDI-TOF MS analysis. 2.0, Man5GlcNAc2; 5.9, (α-Gal)2(β-Gal)2GlcNAc2Man3GlcNAc2.

Similarly, further optimized GFI5.9 glycoengineered P. pastoris strain YGLY3812 was transformed with each of the Influenza HA-containing expression plasmids and colonies were selected on minimal medium containing 300 mg/L Zeocin. Several transformants were selected and cultivated as above. Following Ni-affinity protein purification, PNGase digestion to remove N-glycans, and MALDI-TOF MS analysis. N-glycan masses corresponding to GS5.0, GS5.8 and GS5.9 glycoforms were observed for all Influenza HA proteins tested in ratios similar to other reporter proteins. As an example, N-glycans from Influenza A HA South Carolina expressed in YGLY3812 are shown (FIG. 11).

VIII. Expression of HSV-2 gD protein in a GFI5.9 strain

Figure 12:
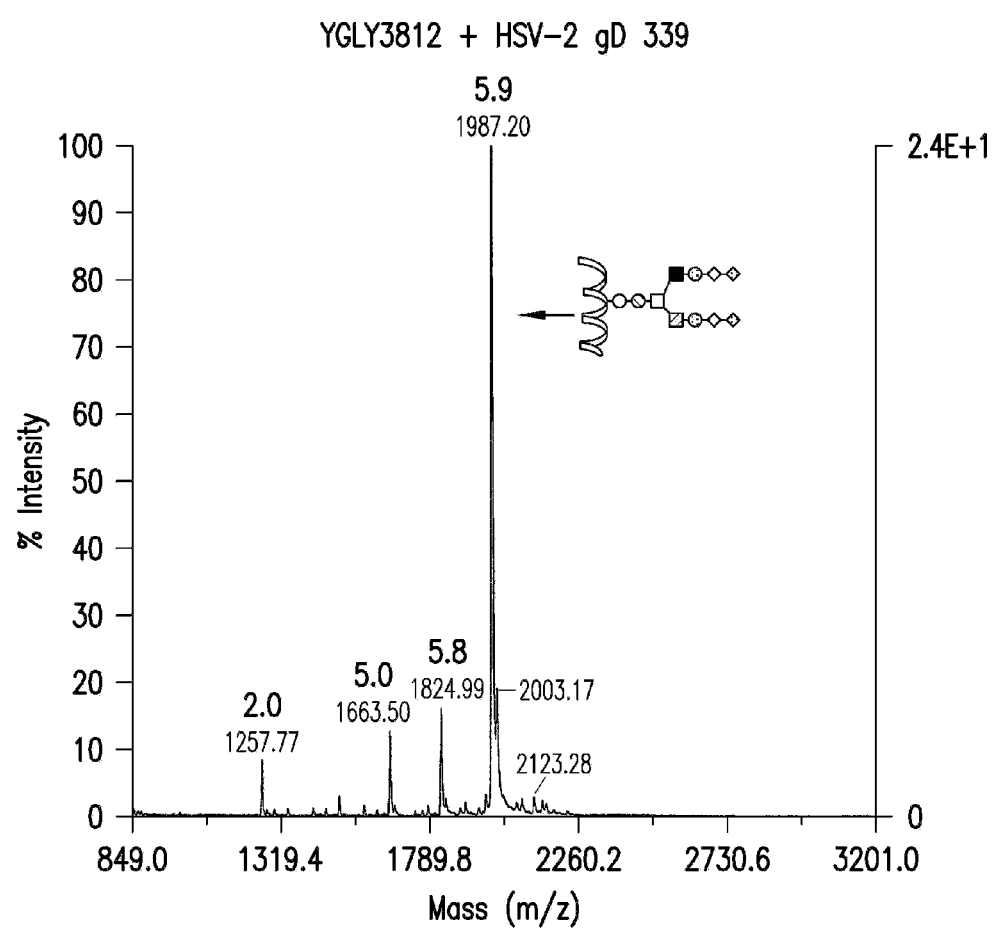
FIG. 12. Expression of HSV-2 gD ectodomain protein in an optimized GFI5.9 glycoengineered *P. pastoris* yeast strain. This strain contains ovine α-1,3-GalT, codon optimized and localization optimized, engineered into an optimized GFI5.0 humanized *P. pastoris* yeast strain. Expression of His-tagged HSV-2 gD ectodomain was demonstrated by Western blot analysis of culture supernatant, then Ni++ affinity chromatography purified protein was subjected to PNGase F digestion and MALDI-TOF MS analysis. 2.0, Man5GlcNAc2; 5.0, (β-Gal)2GlcNAc2Man3GlcNAc2; 5.8, (α-Gal)(β-Gal)2GlcNAc2Man3GlcNAc2; 5.9, (α-Gal)2(β-Gal)2GlcNAc2Man3GlcNAc2.

DNA sequences encoding two different versions of the HSV-2 G strain gD protein ectodomain were synthesized and cloned and named pGLY2757 and pGLY2758 (GeneArt, LLC) [SEQ ID NOS: 5-6]. The two constructs differed by the length of the C-terminus, one encoding the entire ectodomain, amino acids 26-339 (gD 339, pGLY2757) and a second encoding a shorter version without the C-terminal domain, amino acids 26-306 and including two heterologous amino acids, Asn and Gln, appended to the C-terminus after Leu 306 (gD 306NQ, pGLY2758). Each of these plasmids was subcloned into a P. pastoris expression vector containing the AOX1 promoter and ShBLE drug resistance marker and fused in frame with the S. cerevisiae α-Mating Factor pre secretion signal and named pGLY2960 and pGLY2961, respectively. GFI5.9 glycoengineered P. pastoris strain YGLY3812 was transformed with each of the HSV-2 gD-containing expression plasmids and colonies were selected on minimal medium containing 300 mg/L Zeocin. Several transformants were selected and cultivated in 96 well deep well plates for 72 h at 26 C in liquid medium with glycerol as the sole carbon source, then centrifuged and resuspended in medium with methanol as the sole carbon source and incubated at 26 C for 24 hours. Cells were centrifuged and 7 ul of supernatant was subjected to standard Western blot analysis under reducing conditions and probing with a pre-labeled anti-HIS (H3 HIS probe, Santa Cruz) antibody. A band of appropriate size was observed for both of the versions of gD expressed. Approximately 600 ul of supernatant was subjected to Ni-affinity purification, PNGase digestion to remove N-glycans, and MALDI-TOF MS analysis. N-glycan masses corresponding to GS5.8 and GS5.9 glycoforms were observed for both versions of gD with the GS5.9 glycoform as the predominant form (FIG. 12).

IX. Expression of HSV-2 gC protein in a GFI5.9 strain

Figure 13:
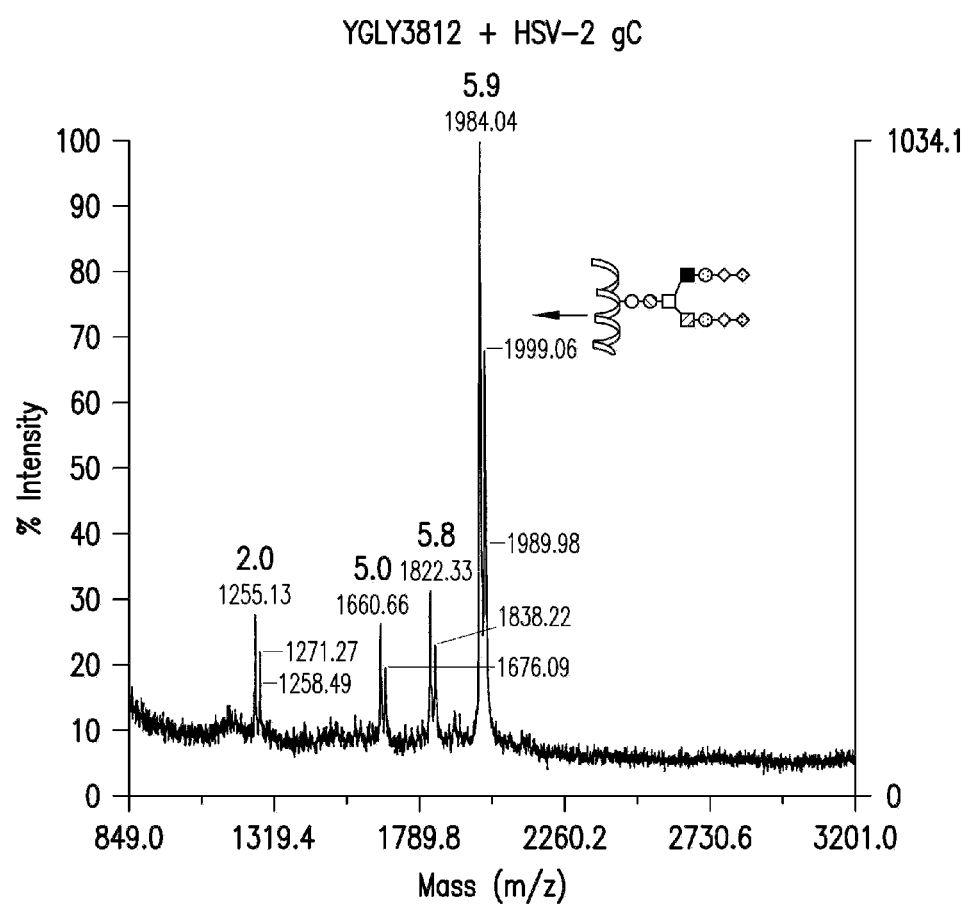
FIG. 13. Expression of HSV-2 gC ectodomain protein in an optimized GFI5.9 glycoengineered *P. pastoris* yeast strain. This strain contains ovine α-1,3-GalT, codon optimized and localization optimized, engineered into an optimized GFI5.0 humanized *P. pastoris* yeast strain. Expression of His-tagged HSV-2 gC ectodomain was demonstrated by Western blot analysis of culture supernatant, then Ni++ affinity chromatography purified protein was subjected to PNGase F digestion and MALDI-TOF MS analysis. 2.0, Man5GlcNAc2; 5.0, (0-Gal)2GlcNAc2Man3GlcNAc2; 5.8, (α-Gal)(β-Gal)2GlcNAc2Man3GlcNAc2; 5.9, (α-Gal)2(β-Gal)2GlcNAc2Man3GlcNAc2.

A DNA sequence encoding the HSV-2 G strain gC protein ectodomain was synthesized and cloned and named pGLY3640 [SEQ ID NO: 7] (GeneArt, Inc., Toronto, CA). The DNA sequence from this plasmid was subcloned into a P. pastoris expression vector containing the AOX1 promoter and ShBLE drug resistance marker and fused in frame with the S. cerevisiae α-Mating Factor pre secretion signal and named pGLY3653. GFI5.9 glycoengineered P. pastoris strain YGLY3812 was transformed with the HSV-2 gC-containing expression plasmid and colonies were selected on minimal medium containing 300 mg/L Zeocin. Several transformants were selected and cultivated in 96 well deep well plates for 72 h at 26 C in liquid medium with glycerol as the sole carbon source, then centrifuged and resuspended in medium with methanol as the sole carbon source and incubated at 26 C for 24 hours. Cells were centrifuged and 7 ul of supernatant was subjected to standard Western blot analysis under reducing conditions and probing with a pre-labeled anti-HIS (H3 HIS probe, Santa Cruz) antibody. A band of appropriate size was observed. Approximately 600 ul of supernatant was subjected to Ni-affinity purification, PNGase digestion to remove N-glycans, and MALDI-TOF MS analysis. N-glycan masses corresponding to GS5.8 and GS5.9 glycoforms were observed with the GS5.9 glycoform as the predominant form (FIG. 13).

REFERENCES

Abdel-Motal et al, J Virology, 80:14, 2006
Abdel-Motal et al., *J. Virology,* 80:6943-6951 (2006)
Abdel-Motal et al, J Virology, 81:17, 2007
Altschul et al., *J. Mol. Biol.* 215:403-410 (1990)
Altschul et al., *Nucleic Acids Res.* 25:3389-3402 (1997)
Anderton et al., Infection and Immunity, 72:2035-2044 (2004)
Ausubel et al., *Current Protocols in Molecular Biology*, Greene Publishing Associates (1992, and Supplements to 2002)
Berenson et al., Infection and Immunity, 73:2728-2735 (2005)
Bodanszky et al., *Peptide Chemistry—A Practical Textbook*, Springer Verlag (1993)
Bobrowicz et al., *Glycobiology;* 14:757-66 (2004)
Bobrowicz, US Patent Application 2006/0211085
*Brucella*: Molecular and Cellular Biology (López-Goñi and Ignacio Moriyón, eds.); Horizon Press (2004)
Bukh et al., WO2000/075337
Caldas et al., Protein Engineering, 13, 353-360 (2000)
Caldwell and Joyce, *PCR Methods Applic.* 2:28-33 (1992)
Camus et al., Microbiology 148:2967-2973 (2002)
Carter et al., J. Virol. 80: 4664-72 (2006)
Casey et al., PNAS, USA; 90:9016-9020 (1993)
Cassataro et al., Infection and Immunity; 73:8079-8088 (2005)
Chang et al., *J. Agric. Food Chem.* 54:815-822 (2006)
Choi et al, *Proc Natl Acad Sci US;* 100:5022-7 (2003)
Cloeckaert et al., Clinical and Diagnostic Laboratory Immunology; 6:627-629 (1999)
Cole et al. Nature 393:537-544 (1998)
Collins, U.S. Pat. No. 6,264,957
Davidson et al., US Patent Application 2006/0040353
Dunn et al., Proc Natl Acad Sci USA, 100:14223-14228 (2003)
Evans et al., *J. Med. Chem.* 30:1229 (1987)
Fauchere, *J. Adv. Drug Res.* 15:29 (1986)
Feldmann, Virus Research 24:1-19 (1992)
Fleischmann and Adams, *Science,* 269:496-512 (1995)
Folks, Nature Medicine 4:16-17 (1998)
Foxwell et al., Microbiol Mol Biol Rev, 62:294-308 (1998)
Galili et al, J Biol Chem, 263:33, 1988
Galili et al, Blood, 82:8, 1993
Galili, U.S. Pat. No. 6,361,775
Gerngross, U.S. Pat. No. 7,029,872
Gerngross et al., US 20040018590
Gish and States, *Nature Genet.* 3:266-272 (1993)
Green et al., Infect Immun 59:3191-3198 (1991)
Grottola et al., Liver Transpl. 8:443-448 (2002)
Hamilton et al, *Science;* 301:1244-6. (2003)
*Handbook of Biochemistry: Section A Proteins*, Vol II, CRC Press (1976); *Essentials of Glycobiology*, Cold Spring Harbor Laboratory Press (1999)
Heermann et al., J. Virology 52:396-402(1984)
Henion et al, *Vaccine,* 15:1174-1182 (1997)
*Immunology—A Synthesis* (Golub and Gren eds., Sinauer Associates, Sunderland, Mass., $2^{nd}$ ed. 1991);
International Committee on Taxonomy of Viruses: The Universal Virus Database, version 3;
Jan et al., Protein Expression and Purification; 7:160-166 (1996)
Jones, *Amino Acid and Peptide Synthesis*, Oxford University Press (1992)
Jung, *Combinatorial Peptide and Nonpeptide Libraries: A Handbook*, John Wiley (1997)
Koch and Koch, The Molecular Biology of Poliovirus. Springer-Verlag/Wein (NY, 1985)
Lamb et al., Proc Natl Acad Sci USA., 78:4170-4174 (1981)
Leung et al., *Technique,* 1:11-15 (1989)
Lo et al., Clinical Infectious Diseases, 36:1246-53 (2003)
Madden et al., *Meth. Enzymol.* 266:131-141 (1996)
Marks et al., *J. Mol. Biol.* 581-596 (1991)
McCauley and Mahy, Biochem. J., 211:281-294 (1983)
McKevitt et al., Infection and Immunity, 73:4445-4450 (2005)
Muerhoff et al., J. Virology 71:6501-6508
Pastrana et al., Virology 337: 365-72 (2005)
Pearson, *Methods Enzymol.* 183:63-98 (1990)
Pyrc et al., Virology J. (2004)
Roizman, Proc Natl Acad Sci USA 93: 11307-11312 (1996)
Roulston et al, Annu Rev Microbiol 53:577-628 (1999)
Russell, J. General Virology 81:2573-2604 (2000)
Salfeld et al., J. Virology 63:798-808 (1989)
Sambrook et al. *Molecular Cloning: A Laboratory Manual,* 2d ed., Cold Spring Harbor Laboratory Press, Cold Spring Harbor, N.Y. (1989)
Schmaljohn et al., J. Gen. Virol. 69:1949-1955 (1988)
Sells et al., PNAS USA 84:1005-1009 (1987)
Svitkin et al., J. Virology; 79:6868-6881 (2005)
*Synthetic Peptides: A Users Guide*, (Grant, ed., W. H. Freeman and Co., 1992)
Taylor and Drickamer, *Introduction to Glycobiology*, Oxford Univ. Press (2003)
Unfer et al., *Cancer Res.,* 63:987-993 (2003)
Veber and Freidinger, *Trends Neurosci.,* 8:392-396 (1985)
Webster et al., J. Histochem Cytochem 54:829-842 (2006)
Whitley and Roizman, J. Clin. Invest. 110(2): 145-151 (2002)
*Worthington Enzyme Manual*, Worthington Biochemical Corp., Freehold, N.J.; *Handbook of Biochemistry: Section A Proteins*, Vol I, CRC Press (1976)
Wu et al, J. Bacteriol. 187:4720-4727 (2005)
Yewdell and Bennink; Annu Rev Cell Dev Biol. 15:579-606 (1999)
Zhang and Madden, *Genome Res.* 7:649-656 (1997)
Zhang et al., Proteomics; 7:1379-1390 (2007).

The invention claimed is:

1. A recombinant *Pichia* host cell producing human-like glycoproteins, comprising a nucleic acid encoding a fusion protein that comprises an α-1, 3 galactosyltransferase catalytic domain fused to a yeast golgi localization peptide which is capable of transferring an α-galactose residue onto a terminal β-galactose residue of an N-linked oligosaccharide branch of an N-glycan having a trimannose core of a glycoprotein produced by the host cell, wherein the N-linked oligosaccharide branch has a structure selected from the group consisting of:

Galβ1, 4-GlcNAcβ1, 2-Manα1, 3;
Galβ1, 4-GlcNAcβ1, 4-Manα1, 3;
Galβ1, 4-GlcNAcβ1, 2-Manα1, 6;

Galβ1, 4-GlcNAcβ1, 4-Manα1, 6; and
Galβ1, 4-GlcNacβ1, 6-Manα1, 6.

2. The recombinant *Pichia* host cell of claim 1 which is *Pichia pastoris*.

3. The recombinant *Pichia* host cell of claim 1 wherein the yeast golgi localization peptide is a *Saccharomyces cerevisiae* Mnn2p transmembrane Golgi targeting localization domain.

4. A recombinant *Pichia* host cell producing human-like glycoproteins, comprising a nucleic acid encoding a fusion protein that comprises a *Mus Musculus* α-1, 3 -galactosyl transferase that lacks a putative transmembrane Golgi localization domain, which is fused to a *Saccharomyces cerevisiae* Mnn2p transmembrane Golgi targeting localization domain, which is capable of transferring an α-galactose residue onto a terminal β-galactose residue of an N-linked oligosaccharide branch of an N-glycan having a trimannose core of a glycoprotein produced by the host cell, wherein the N-linked oligosaccharide branch has a structure selected from the group consisting of:
Galβ1, 4-GlcNAcβ1, 2-Manα1, 3;
Galβ1, 4-GlcNAcβ1, 4-Manα1, 3;
Galβ1, 4-GlcNAcβ1, 2-Manα1, 6;
Galβ1, 4-GlcNAcβ1, 4-Manα1, 6; and
Galβ1, 4-GlcNacβ1, 6-Manα1, 6.

5. The recombinant *Pichia* host cell of claim 4 which lacks sialyltransferase.

6. The recombinant *Pichia* host cell of claim 4 which is *Pichia pastoris*.

* * * * *

SEQUENCE LISTING

```
<160> NUMBER OF SEQ ID NOS: 7

<210> SEQ ID NO 1
<211> LENGTH: 34
<212> TYPE: DNA
<213> ORGANISM: Mus musculus
```

-continued

<400> SEQUENCE: 1
ttggcgcgcc aacagcccag acggctcttt cttg                                    34

<210> SEQ ID NO 2
<211> LENGTH: 34
<212> TYPE: DNA
<213> ORGANISM: Mus musculus

<400> SEQUENCE: 2
ggttaattaa tcagacatta tttctaacca aatt                                    34

<210> SEQ ID NO 3
<211> LENGTH: 562
<212> TYPE: PRT
<213> ORGANISM: Influenza

<400> SEQUENCE: 3

```
Gln Asp Leu Pro Gly Asn Asp Asn Ser Thr Ala Thr Leu Cys Leu Gly
  1               5                  10                  15

His His Ala Val Pro Asn Gly Thr Leu Val Lys Thr Ile Thr Asp Asp
             20                  25                  30

Gln Ile Glu Val Thr Asn Ala Thr Glu Leu Val Gln Ser Ser Ser Thr
         35                  40                  45

Gly Lys Ile Cys Asn Asn Pro His Arg Ile Leu Asp Gly Ile Asp Cys
     50                  55                  60

Thr Leu Ile Asp Ala Leu Leu Gly Asp Pro His Cys Asp Val Phe Gln
 65                  70                  75                  80

Asn Glu Thr Trp Asp Leu Phe Val Glu Arg Ser Lys Ala Phe Ser Asn
                 85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Val His His Pro Ser Thr Asn Gln Glu Gln Thr
            180                 185                 190

Ser Leu Tyr Val Gln Ala Ser Gly Arg Val Thr Val Ser Thr Arg Arg
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300
```

```
Cys Pro Lys Tyr Val Lys Gln Asn Thr Leu Lys Leu Ala Thr Gly Met
305                 310                 315                 320

Arg Asn Val Pro Glu Lys Gln Thr Arg Gly Leu Phe Gly Ala Ile Ala
            325                 330                 335

Gly Phe Ile Glu Asn Gly Trp Glu Gly Met Ile Asp Gly Trp Tyr Gly
            340                 345                 350

Phe Arg His Gln Asn Ser Glu Gly Thr Gly Gln Ala Ala Asp Leu Lys
            355                 360                 365

Ser Thr Gln Ala Ala Ile Asp Gln Ile Asn Gly Lys Leu Asn Arg Val
370                 375                 380

Ile Glu Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
            405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
            435                 440                 445

Glu Lys Thr Arg Arg Gln Leu Arg Glu Asn Ala Glu Asp Met Gly Asn
450                 455                 460

Gly Cys Phe Lys Ile Tyr His Lys Cys Asp Asn Ala Cys Ile Glu Ser
465                 470                 475                 480

Ile Arg Asn Gly Thr Tyr Asp His Asp Val Tyr Arg Asp Glu Ala Leu
            485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
            515                 520                 525

Val Val Leu Leu Gly Phe Ile Met Trp Ala Cys Gln Arg Gly Asn Ile
            530                 535                 540

Arg Cys Asn Ile Cys Ile Gly Gly His His His His His His
545                 550                 555                 560

His His

<210> SEQ ID NO 4
<211> LENGTH: 525
<212> TYPE: PRT
<213> ORGANISM: Influenza

<400> SEQUENCE: 4

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Lys Leu Lys Gly Ile Ala
            35                  40                  45

Pro Leu Gln Leu Gly Lys Cys Asn Ile Ala Gly Trp Leu Leu Gly Asn
50                  55                  60

Pro Glu Cys Asp Leu Leu Leu Thr Ala Ser Ser Trp Ser Tyr Ile Val
65                  70                  75                  80

Glu Thr Ser Asn Ser Glu Asn Gly Thr Cys Tyr Pro Gly Asp Phe Ile
            85                  90                  95

Asp Tyr Glu Glu Leu Arg Glu Gln Leu Ser Ser Val Ser Ser Phe Glu
            100                 105                 110
```

-continued

```
Lys Phe Glu Ile Phe Pro Lys Thr Ser Ser Trp Pro Asn His Glu Thr
            115                 120                 125
Thr Lys Gly Val Thr Ala Ala Cys Ser Tyr Ala Gly Ala Ser Ser Phe
        130                 135                 140
Tyr Arg Asn Leu Leu Trp Leu Thr Lys Lys Gly Ser Ser Tyr Pro Lys
145                 150                 155                 160
Leu Ser Lys Ser Tyr Val Asn Asn Lys Gly Lys Glu Val Leu Val Leu
                165                 170                 175
Trp Gly Val His His Pro Pro Thr Gly Thr Asp Gln Gln Ser Leu Tyr
            180                 185                 190
Gln Asn Ala Asp Ala Tyr Val Ser Val Gly Ser Ser Lys Tyr Asn Arg
        195                 200                 205
Arg Phe Thr Pro Glu Ile Ala Ala Arg Pro Lys Val Arg Asp Gln Ala
    210                 215                 220
Gly Arg Met Asn Tyr Tyr Trp Thr Leu Leu Glu Pro Gly Asp Thr Ile
225                 230                 235                 240
Thr Phe Glu Ala Thr Gly Asn Leu Ile Ala Pro Trp Tyr Ala Phe Ala
                245                 250                 255
Leu Asn Arg Gly Ser Gly Ser Gly Ile Ile Thr Ser Asp Ala Pro Val
            260                 265                 270
His Asp Cys Asn Thr Lys Cys Gln Thr Pro His Gly Ala Ile Asn Ser
        275                 280                 285
Ser Leu Pro Phe Gln Asn Ile His Pro Val Thr Ile Gly Glu Cys Pro
    290                 295                 300
Lys Tyr Val Arg Ser Thr Lys Leu Arg Met Ala Thr Gly Leu Arg Asn
305                 310                 315                 320
Ile Pro Ser Ile Gln Ser Arg Gly Leu Phe Gly Ala Ile Ala Gly Phe
                325                 330                 335
Ile Glu Gly Gly Trp Thr Gly Met Ile Asp Gly Trp Tyr Gly Tyr His
            340                 345                 350
His Gln Asn Glu Gln Gly Ser Gly Tyr Ala Ala Asp Gln Lys Ser Thr
        355                 360                 365
Gln Asn Ala Ile Asp Gly Ile Thr Asn Lys Val Asn Ser Val Ile Glu
    370                 375                 380
Lys Met Asn Thr Gln Phe Thr Ala Val Gly Lys Glu Phe Asn Asn Leu
385                 390                 395                 400
Glu Arg Arg Ile Glu Asn Leu Asn Lys Lys Val Asp Asp Gly Phe Leu
                405                 410                 415
Asp Ile Trp Thr Tyr Asn Ala Glu Leu Leu Val Leu Leu Glu Asn Glu
            420                 425                 430
Arg Thr Leu Asp Phe His Asp Ser Asn Val Arg Asn Leu Tyr Glu Lys
        435                 440                 445
Val Lys Ser Gln Leu Lys Asn Asn Ala Lys Glu Ile Gly Asn Gly Cys
    450                 455                 460
Phe Glu Phe Tyr His Lys Cys Asp Asp Ala Cys Met Glu Ser Val Arg
465                 470                 475                 480
Asn Gly Thr Tyr Asp Tyr Pro Lys Tyr Ser Glu Glu Ser Lys Leu Asn
                485                 490                 495
Arg Glu Glu Ile Asp Gly Val Lys Leu Glu Ser Met Gly Val Tyr Gln
            500                 505                 510
Ile Gly Gly Gly His His His His His His
            515                 520                 525
```

<210> SEQ ID NO 5
<211> LENGTH: 326
<212> TYPE: PRT
<213> ORGANISM: Herpes simplex virus

<400> SEQUENCE: 5

Lys Tyr Ala Leu Ala Asp Pro Ser Leu Lys Met Ala Asp Pro Asn Arg
 1               5                  10                  15

Phe Arg Gly Lys Asn Leu Pro Val Leu Asp Gln Leu Thr Asp Pro Pro
            20                  25                  30

Gly Val Lys Arg Val Tyr His Ile Gln Pro Ser Leu Glu Asp Pro Phe
        35                  40                  45

Gln Pro Pro Ser Ile Pro Ile Thr Val Tyr Tyr Ala Val Leu Glu Arg
    50                  55                  60

Ala Cys Arg Ser Val Leu Leu His Ala Pro Ser Glu Ala Pro Gln Ile
65                  70                  75                  80

Val Arg Gly Ala Ser Asp Glu Ala Arg Lys His Thr Tyr Asn Leu Thr
                85                  90                  95

Ile Ala Trp Tyr Arg Met Gly Asp Asn Cys Ala Ile Pro Ile Thr Val
            100                 105                 110

Met Glu Tyr Thr Glu Cys Pro Tyr Asn Lys Ser Leu Gly Val Cys Pro
        115                 120                 125

Ile Arg Thr Gln Pro Arg Trp Ser Tyr Tyr Asp Ser Phe Ser Ala Val
    130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Arg Ala Ser Cys Lys Tyr Ala
            180                 185                 190

Leu Pro Leu Arg Ile Pro Pro Ala Ala Cys Leu Thr Ser Lys Ala Tyr
        195                 200                 205

Gln Gln Gly Val Thr Val Asp Ser Ile Gly Met Leu Pro Arg Phe Ile
    210                 215                 220

Pro Glu Asn Gln Arg Thr Val Ala Leu Tyr Ser Leu Lys Ile Ala Gly
225                 230                 235                 240

Trp His Gly Pro Lys Pro Pro Tyr Thr Ser Thr Leu Leu Pro Pro Glu
                245                 250                 255

Leu Ser Asp Thr Thr Asn Ala Thr Gln Pro Glu Leu Val Pro Glu Asp
            260                 265                 270

Pro Glu Asp Ser Ala Leu Leu Glu Asp Pro Ala Gly Thr Val Ser Ser
        275                 280                 285

Gln Ile Pro Pro Asn Trp His Ile Pro Ser Ile Gln Asp Val Ala Pro
    290                 295                 300

His His Ala Pro Ala Ala Pro Ser Asn Pro Gly Gly His His His
305                 310                 315                 320

His His His His His His
            325

<210> SEQ ID NO 6
<211> LENGTH: 295
<212> TYPE: PRT
<213> ORGANISM: Herpes simplex virus

<400> SEQUENCE: 6

```
Lys Tyr Ala Leu Ala Asp Pro Ser Leu Lys Met Ala Asp Pro Asn Arg
 1               5                  10                  15

Phe Arg Gly Lys Asn Leu Pro Val Leu Asp Gln Leu Thr Asp Pro Pro
             20                  25                  30

Gly Val Lys Arg Val Tyr His Ile Gln Pro Ser Leu Glu Asp Pro Phe
         35                  40                  45

Gln Pro Pro Ser Ile Pro Ile Thr Val Tyr Tyr Ala Val Leu Glu Arg
 50                  55                  60

Ala Cys Arg Ser Val Leu Leu His Ala Pro Ser Glu Ala Pro Gln Ile
 65                  70                  75                  80

Val Arg Gly Ala Ser Asp Glu Ala Arg Lys His Thr Tyr Asn Leu Thr
                 85                  90                  95

Ile Ala Trp Tyr Arg Met Gly Asp Asn Cys Ala Ile Pro Ile Thr Val
            100                 105                 110

Met Glu Tyr Thr Glu Cys Pro Tyr Asn Lys Ser Leu Gly Val Cys Pro
            115                 120                 125

Ile Arg Thr Gln Pro Arg Trp Ser Tyr Tyr Asp Ser Phe Ser Ala Val
        130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Arg Ala Ser Cys Lys Tyr Ala
            180                 185                 190

Leu Pro Leu Arg Ile Pro Pro Ala Ala Cys Leu Thr Ser Lys Ala Tyr
        195                 200                 205

Gln Gln Gly Val Thr Val Asp Ser Ile Gly Met Leu Pro Arg Phe Ile
    210                 215                 220

Pro Glu Asn Gln Arg Thr Val Ala Leu Tyr Ser Leu Lys Ile Ala Gly
225                 230                 235                 240

Trp His Gly Pro Lys Pro Pro Tyr Thr Ser Thr Leu Leu Pro Pro Glu
                245                 250                 255

Leu Ser Asp Thr Thr Asn Ala Thr Gln Pro Glu Leu Val Pro Glu Asp
            260                 265                 270

Pro Glu Asp Ser Ala Leu Leu Glu Asp Asn Gln Gly Gly Gly His His
        275                 280                 285

His His His His His
        290             295

<210> SEQ ID NO 7
<211> LENGTH: 437
<212> TYPE: PRT
<213> ORGANISM: Herpes simplex virus

<400> SEQUENCE: 7

Leu Ala Asn Ala Ser Pro Gly Arg Thr Ile Thr Val Gly Pro Arg Gly
 1               5                  10                  15

Asn Ala Ser Asn Ala Ala Pro Ser Ala Ser Pro Arg Asn Ala Ser Ala
             20                  25                  30

Pro Arg Thr Thr Pro Thr Pro Pro Gln Pro Arg Lys Ala Thr Lys Ser
         35                  40                  45

Lys Ala Ser Thr Ala Lys Pro Ala Pro Pro Lys Thr Gly Pro Pro
 50                  55                  60

Lys Thr Ser Ser Glu Pro Val Arg Cys Asn Arg His Asp Pro Leu Ala
 65                  70                  75                  80
```

```
Arg Tyr Gly Ser Arg Val Gln Ile Arg Cys Arg Phe Pro Asn Ser Thr
                85                  90                  95

Arg Thr Glu Phe Arg Leu Gln Ile Trp Arg Tyr Ala Thr Ala Thr Asp
            100                 105                 110

Ala Glu Ile Gly Thr Ala Pro Ser Leu Glu Glu Val Met Val Asn Val
        115                 120                 125

Ser Ala Pro Pro Gly Gly Gln Leu Val Tyr Asp Ser Ala Pro Asn Arg
    130                 135                 140

Thr Asp Pro His Val Ile Trp Ala Glu Gly Ala Gly Pro Gly Ala Ser
145                 150                 155                 160

Pro Arg Leu Tyr Ser Val Val Gly Pro Leu Gly Arg Gln Arg Leu Ile
                165                 170                 175

Ile Glu Glu Leu Thr Leu Glu Thr Gln Gly Met Tyr Tyr Trp Val Trp
            180                 185                 190

Gly Arg Thr Asp Arg Pro Ser Ala Tyr Gly Thr Trp Val Arg Val Arg
        195                 200                 205

Val Phe Arg Pro Pro Ser Leu Thr Ile His Pro His Ala Val Leu Glu
    210                 215                 220

Gly Gln Pro Phe Lys Ala Thr Cys Thr Ala Ala Thr Tyr Tyr Pro Gly
225                 230                 235                 240

Asn Arg Ala Glu Phe Val Trp Phe Glu Asp Gly Arg Arg Val Phe Asp
                245                 250                 255

Pro Ala Gln Ile His Thr Gln Thr Gln Glu Asn Pro Asp Gly Phe Ser
            260                 265                 270

Thr Val Ser Thr Val Thr Ser Ala Ala Val Gly Gly Gln Gly Pro Pro
        275                 280                 285

Arg Thr Phe Thr Cys Gln Leu Thr Trp His Arg Asp Ser Val Ser Phe
    290                 295                 300

Ser Arg Arg Asn Ala Ser Gly Thr Ala Ser Val Leu Pro Arg Pro Thr
305                 310                 315                 320

Ile Thr Met Glu Phe Thr Gly Asp His Ala Val Cys Thr Ala Gly Cys
                325                 330                 335

Val Pro Glu Gly Val Thr Phe Ala Trp Phe Leu Gly Asp Asp Ser Ser
            340                 345                 350

Pro Ala Glu Lys Val Ala Val Ala Ser Gln Thr Ser Cys Gly Arg Pro
        355                 360                 365

Gly Thr Ala Thr Ile Arg Ser Thr Leu Pro Val Ser Tyr Glu Gln Thr
    370                 375                 380

Glu Tyr Ile Cys Arg Leu Ala Gly Tyr Pro Asp Gly Ile Pro Val Leu
385                 390                 395                 400

Glu His His Gly Ser His Gln Pro Pro Arg Asp Pro Thr Glu Arg
                405                 410                 415

Gln Val Ile Arg Ala Ile Glu Gly Arg Gly Gly His His His
            420                 425                 430

His His His His His
        435
```